United States Patent [19]

Rapaport et al.

[11] Patent Number: 5,926,526
[45] Date of Patent: Jul. 20, 1999

[54] METHOD AND APPARATUS FOR AUTOMATED PATIENT INFORMATION RETRIEVAL

[75] Inventors: Seymour A. Rapaport, 1050 Crooked Creek Dr., Los Altos, Calif. 94024; Jeffrey A. Rapaport, 362 West Olive Ave. #16, Sunnyvale, Calif. 94086; Stanley L. Rapaport, Manitou Springs, Colo.; Terry A. Jackson, Dublin; Kent Don, Palo Alto, both of Calif.

[73] Assignees: Seymour A. Rapaport, Los Altos, Calif.; Jeffrey A. Rapaport, Sunnyvale, Calif.

[21] Appl. No.: 08/581,749

[22] Filed: Dec. 29, 1995

[51] Int. Cl.⁶ .................................................... H04M 3/00
[52] U.S. Cl. ..................................... 379/88.25; 379/88.22
[58] Field of Search .................................. 379/38, 67, 69, 379/88, 89, 111, 114, 88.22, 88.23, 88.25

[56] References Cited

U.S. PATENT DOCUMENTS

| | | | |
|---|---|---|---|
| 4,060,848 | 11/1977 | Hyatt | 340/172.5 |
| 4,581,486 | 4/1986 | Matthews et al. | 379/88 |
| 4,802,008 | 1/1989 | Walling | 358/141 |
| 4,996,704 | 2/1991 | Brunson | 379/67 |
| 5,146,487 | 9/1992 | Bergsman et al. | 379/89 |
| 5,260,986 | 11/1993 | Pershan | 379/67 |
| 5,325,294 | 6/1994 | Keene | 379/95 |
| 5,353,259 | 10/1994 | Howes et al. | 369/25 |
| 5,355,406 | 10/1994 | Chencinski et al. | 379/88 |
| 5,369,697 | 11/1994 | Murray et al. | 379/361 |
| 5,388,151 | 2/1995 | Khalid et al. | 379/67 |
| 5,402,472 | 3/1995 | MeLampy et al. | 379/67 |
| 5,406,557 | 4/1995 | Baudoin | 370/61 |
| 5,425,078 | 6/1995 | Stern | 379/67 |
| 5,430,791 | 7/1995 | Feit et al. | 379/67 |
| 5,432,844 | 7/1995 | Core et al. | 379/67 |
| 5,479,487 | 12/1995 | Hammond | 379/89 |
| 5,497,373 | 3/1996 | Hulen et al. | 379/89 |
| 5,509,064 | 4/1996 | Welner et al. | 379/67 |

OTHER PUBLICATIONS

Kaiser Permanente.
Med–Connect.
Middleton, "Service lets patient dial a doctor", Richmond Times–Dispatch, Aug. 1995.

*Primary Examiner*—Daniel S. Hunter
*Attorney, Agent, or Firm*—Fliesler, Dubb, Meyer & Lovejoy LLP

[57] ABSTRACT

A automated patient information retrieval system is provided for notifying patients of medical information. The automated patient information retrieval system includes a processor coupled to memory and a telephone interface circuitry. A processor is also coupled to a modem and an I/O interface. The system allows for a medical provider to enter medical information into voice mailboxes. The messages many be time-sensitive wherein the system automatically calls patients to notify of pending medical information in voice mailboxes. The patient then may telephone the system to receive a medical message stored in a patient mailbox. Medical providers may generate custom voice messages or enter predetermined bulletin codes associated with pre-recorded voice messages. Also, medical providers can enter notes associated with medical voice mailboxes which are only accessible by the medical provider. Message integrity and security are enhanced by requiring the patient to enter both a patient identification number and a medical provider identification number.

26 Claims, 16 Drawing Sheets

METHOD AND APPARATUS FOR AUTOMATED PATIENT INFORMATION RETRIEVAL

BACKGROUND OF INVENTION

1. Field of the Invention

The present invention relates to providing medical information, and more particularly, to providing medical information, such as laboratory test results, to patients.

2. Background of the Invention

Medical providers, for example physicians or medical assistants, often must notify patients of medical information. This medical information may include laboratory test results and may also include advisory information. The medical information provided to patients may consist of a relatively simple message, such as "your pregnancy test is negative" to a rather complex message, such as "your hemoglobin A1C test is 8.1; this is good control." Various medical laboratory tests may take from a few hours to multiple days before the information is available to the medical provider and thus, the patient. Once the information is available, medical providers are responsible for notifying the patient of the medical information. At times, the test results may be normal; while at other times, medical tests may require immediate notification and further action. Test results may reveal a life threatening condition which requires immediate treatment.

However, presently, medical providers waste valuable time and resources in attempting to contact patients with medical information. The patient may not be available at the time the medical provider attempts to contact the patient by telephone. Further, medical providers are unable to leave medical information or test results with third parties or on patients' answering machines. The medical provider must ensure that the medical information remains confidential and that the patient's privacy is respected. If a message to contact the medical provider is left on an answering machine or with a third party, the patient may have difficulty in contacting a medical provider by telephone. Thus, valuable medical provider time and resources are wasted in an attempt to provide medical information to patients.

Furthermore, it is necessary for medical providers to confirm that patients actually receive the medical information. As described above, the medical information could inform a patient of a life threatening condition. If the medical provider does not provide the information, the medical provider could be exposed to liability in failing to inform a patient of a medical condition.

Therefore, it is desirable to provide a method and apparatus for providing medical information to patients without wasting medical provider, as well as patient, time and resources. Medical providers should be able to create generic, as well as specific, messages to patients without having to attempt to contact patients numerous times.

The method and apparatus should also alert medical providers that patients have not received medical information, as well as confirm the receipt of messages by patients. The alerts or confirmations should be in written or tangible form. The method and apparatus should insure patient confidentiality and privacy. Finally, the method and apparatus should be easy to use and have the capacity to train medical providers on its use.

SUMMARY OF INVENTION

According to the present invention, a method for creating a medical voice message in an automated patient information retrieval system is provided. A medical voice message is generated in a mailbox responsive to a selected code. A title associated with the medical voice message and a patient name can be played.

According to another aspect of the present invention, a method for accessing the medical voice message in an automated patient information retrieval system comprises the step of entering a bulletin code and making a determination as to what type of message is associated with the bulletin code. A voice message is then generated responsive to the determined message type. The message type may be 1) a system prerecorded bulletin; 2) personal prerecorded bulletin; 3) on the fly bulletin; or 4) medical provider note. The method further comprises the step of entering to edit mode responsive to the determined message type.

According to another aspect of the present invention, the method further comprises a step of generating a plurality of voice messages in a plurality of mailboxes responsive to a bulletin code.

According to another aspect of the present invention, a method for providing a medical voice message in a medical message delivery system comprises the step of providing a mailbox and generating a medical voice message in the mailbox accessible by a recipient. A voice message note may be then generated associated with a medical voice message accessible by only a predetermined individual or medical provider.

According to still another aspect of the present invention, a method for contacting a medical voice message recipient of pending medical voice messages in an automatic patient information retrieval system is provided. The steps comprise providing a mailbox and generating a medical voice message in the mailbox. A medical voice message recipient is telephoned at a predetermined telephone number and a voice message notifying recipient to receive the medical voice message in the mailbox is generated.

According to still another aspect of the present invention, a method for alerting a medical provider of the reception of a voice message by a patient in an automatic patient information retrieval system is provided. A medical voice message is generated in a mailbox. A selected time period for receiving the medical voice message by the patient is set and an alert signal is generated to the medical provider responsive to the time period and the reception of the voice message.

According to still another aspect of the present invention, a method for insuring medical voice message security in an automated patient information retrieval system comprises the step of receiving a first signal representing the medical provider code and comparing the medical provider code with a predetermined medical provider code. A second signal representing a patient mailbox code is then received and compared to a predetermined patient code.

According to still a further aspect of the present invention, an automated patient information retrieval system comprising a processing unit and voice mailbox is provided. The system further comprises a memory location coupled to the processing unit and a program stored in a memory location containing a code associated with a medical voice message. The program directs the processing unit to create an associated medical voice message in the mailbox responsive to a signal representing the code.

According to another aspect of the present invention, an automated patient information retrieval system comprises a processing unit, a first memory location coupled to the processing unit, and a second memory location coupled to the processing unit. The first memory location stores a medical mailbox having a medical message which is pending receipt and has been created within a predetermined period of time. The second memory location stores a medical mailbox having a medical message which has been received within the predetermined period of time.

According to another aspect of the present invention, an apparatus for retrieving medical information is provided. The apparatus comprises a processing unit and a video circuit providing a video signal coupled to a memory location. A program is stored in the memory location containing a code associated with a video medical message. The program directs the processing unit and the video circuit to generate a video signal representing the medical video image responsive to a selected code. The apparatus further comprises input means coupled to the process unit for inputting the selected code. A video display device is also coupled to the processing unit for displaying the medical video image. The medical video image includes information regarding test results and medical health information. The medical video image may include text and speech.

DETAILED DESCRIPTION OF THE INVENTION

Figure 1:
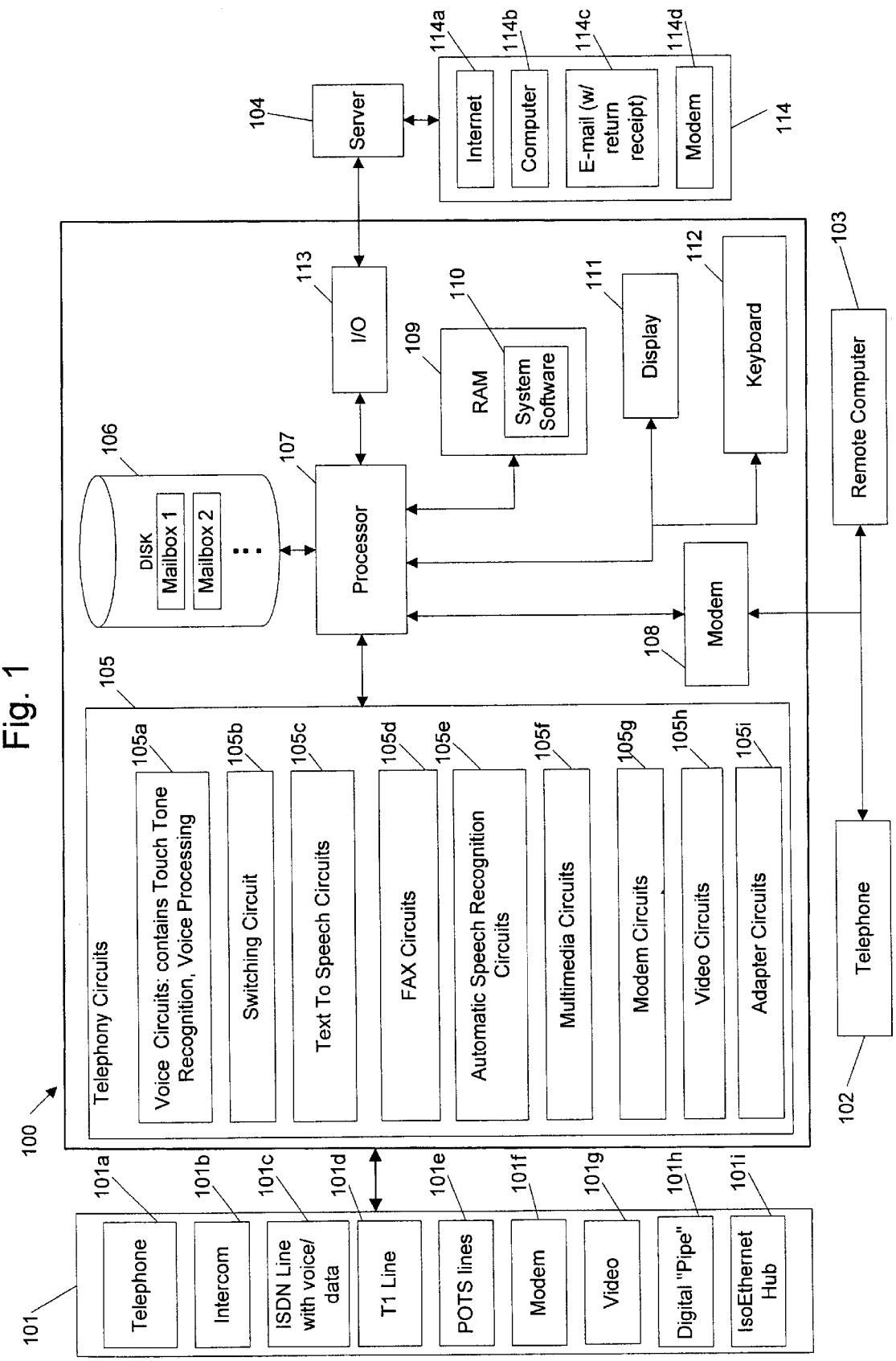
FIG. 1 illustrates a simplified hardware block diagram of the automated patient information retrieval system according to the present invention.
Figure 10:
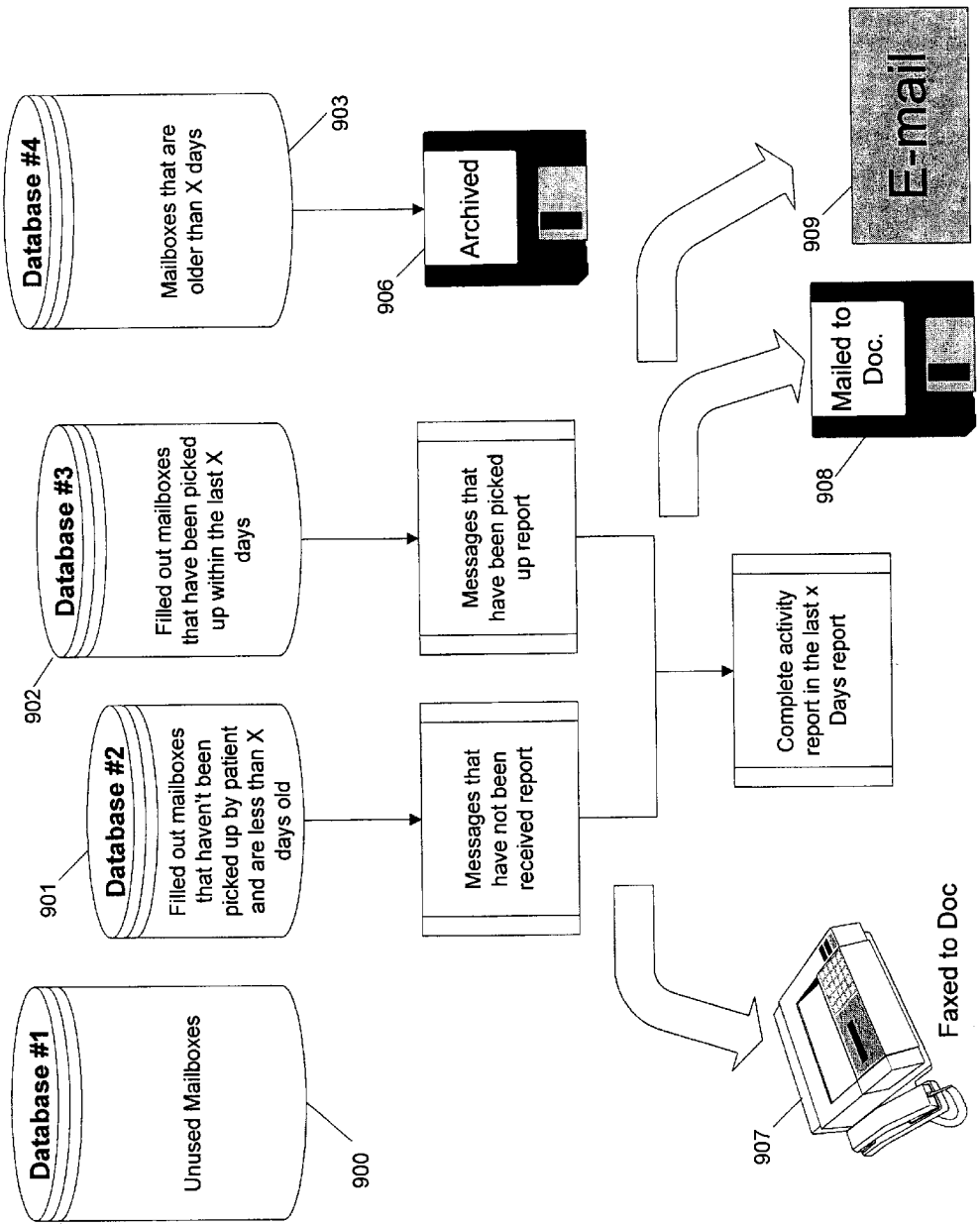
FIG. 10 illustrates a database architecture in an automated patient information retrieval system according to the present invention.

FIG. 1 illustrates an automated patient information retrieval system ("system") 100 according to the present invention. In an embodiment, system 100 includes processor 107. In a preferred embodiment, processor 107 is a 486 DX2-80 microprocessor. Processor 107 is coupled to telephony circuits 105, disc 106, Random Access Memory ("RAM") 109, modem 108, I/O interface 113, display 111 and keyboard 112. In a preferred embodiment, disc 106 will be an 850 megabyte hard disc drive providing approximately 80 hours of voicemail storage. In another embodiment, FIG. 10 illustrates an alternate disc 106 architecture. Disc 106 contains numerous used and unused mailboxes which may contain medical information for patients. Disc 106 also includes prerecorded voice messages and prompts. In still another alternate embodiment, a mailbox may be information stored in a data file.

In an embodiment, modem 108 would be a 28.8K baud rate modem, which provides remote access to system 100 for service and maintenance from telephone 102 and remote computer 103.

RAM 109, in an embodiment, includes 8 megabytes of RAM. RAM 109 also includes VOS™ software supplied by Parity Software, located at 870 Market Street, Suite 1155, San Francisco, Calif., DOS 6.22 software, communications software, and system software 110. VOS™ software interacts with processor 107 and telephony circuits 105 to handle, for example, voice recognition, faxing, voice processing and text to speech processing. System software 110 is primarily responsible for operating the automatic patient information retrieval system 100. Flow charts, FIGS. 2–9 which are described in detail below, illustrate the operation of system 100.

Patients, or those interested in obtaining medical information, as well as medical providers, access system 100 from telephone 101a and other devices generally referred to as input/output devices 101 which are coupled to telephony circuits 105.

For example, input/output device 101 may be a standard touchtone telephone 101a. However, the network transport may be intercom circuits 101b, ISDN lines (Integrated Services Digital Network) 101c, T1 lines 101d, POTS lines 101e, modem lines 101f, video lines 101g, digital "pipes" 101h and Ethernet Hub 101i. Advanced network information such as Automatic Number Identification ("ANI") (also known as caller ID) and Dialed Number Identification Service ("DNIS") will be passed by the network and recognized by system 100. ANI or DNIS may be used to identify a medical provider accessing system 100. In an embodiment, this may be used to identify medical provider and/or patient.

Telephony circuits 105 include, among other circuits, circuits for interfacing with input/output devices 101. These circuits include a voice circuit 105a having a touch tone recognition circuit and voice processing circuit, as well as other functions. Other circuits include switching circuits 105b, text to speech circuits 105c, facsimile ("fax") circuits 105d, automatic speech recognition circuits 105e, multimedia circuits 105f, modem circuits 105g, video circuits 105h, and adapter circuits 105i. These circuits enable patients or others to input information by way of touch tones, pulses, voice, video, or equivalents thereof. Other input and output devices for accessing system 100 could also include television signals, wireless communication devices, internet devices and electronic mail devices. In alternate embodiments, voice recognition signatures could be recognized by system 100 using speech recognition circuits 105e.

Figure 11:
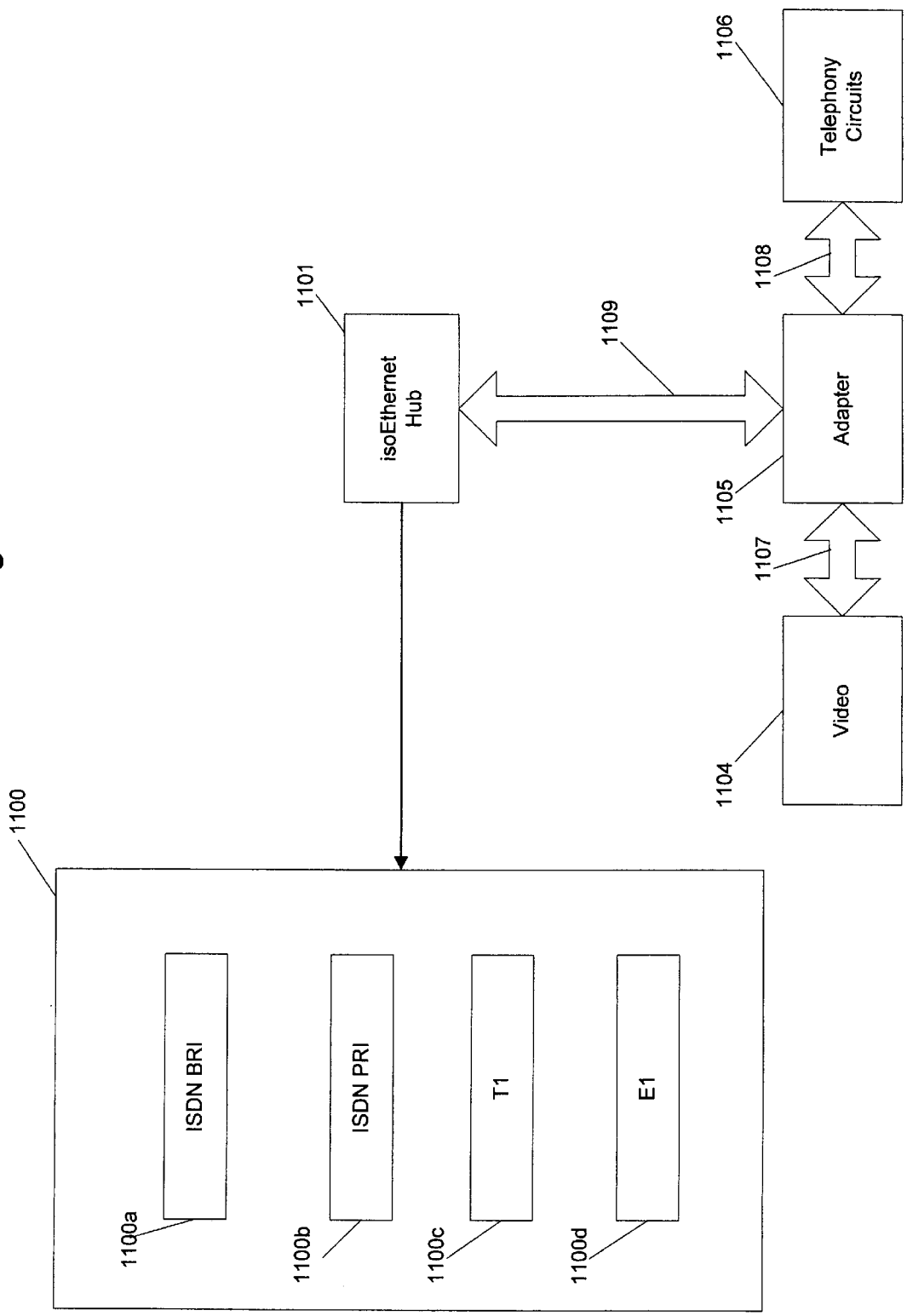
FIG. 11 illustrates providing video and telephony through an isoEthernet Hub accessible via ISDN, T1 and/or E1 pipes in an automated patient information retrieval system according to the present invention.

FIG. 11, illustrates an embodiment of telephony circuits 105. In particular FIG. 11 illustrates providing video medical information. Circuit 1100 includes circuits, 1100a, 1100b, 1100c and 1100d which are used as input/output devices 101. In an embodiment, circuit 1100a is an ISDN BRI circuit capable of handling 128 K audio/video transmission, 1100b is an ISDN BRI (US or European) circuit capable of handling 128K audio/video transmission, circuit 1100c is a T1 line, circuit 1100d is an E1 line.

Circuit 1101 is coupled to circuit 1100 and, in an embodiment, is an isoEthernet hub that can support 96 simultaneous two-way channels to a wide area network (WAN). Voice and/or video may be transported in a Local Area Network ("LAN") and Wide Area Network ("WAN") access is by either using the bus (video) parts or parts on the telephony circuits 1106, described below.

In an embodiment, video circuit 1104, adapter 1105 and telephony circuit 1106 are used in telephony circuits 105. In an embodiment, Adaptor circuit 1105 interfaces to existing telephone lines 1109 using a QuickNet SC-ISO adapter supplied by QuickNet Technologies, Inc., located at 324 Ritch Street, San Francisco, Calif. 94107. Circuit 1104 is a VCON Armada for 128K bit video conferencing 4.320 format. VCON Armada is supplied by VCON Inc., 5000 Quorm Drive Suite 700, Dallas, Tex. 75240. This circuit can be used for station to station transmission of data or from station to WAN or from WAN to station. Circuit 1106 are telephony circuits.

Circuit 1104 is coupled to adapter 1105 by circuit 1107, an Multi Vendor Integration Protocol ("MVIP") connect, that connects video circuits 1104 with an adapter circuit 1105. Adapter circuit 1105 is coupled to telephony circuits 1106 by circuit 1108, an Signal Computer ("SC") bus or PEB connector. Software for these hardware devices will be stored in RAM 109 and include Telephone Application Program Interface ("TAPI") driver, Dialogic SC Drivers, VOS™ Software and Drivers, QuickNet SC-ISO adapter drivers, VCON Armada drives, as well as the telephony drivers.

In another embodiment telephony circuits 105 includes a DIALOGIC VRX/40 faxcard with a VoiceView firmware support package. VoiceView is supplied by Radish Communications Systems, Inc. P.O. Box 20220, Boulder, Colo. A Unix Package SCO is stored in RAM 109 as well as Dialogic System drivers and VoiceView drivers for Unix, VOS™ Software and driver for Unix, and a VoiceView server API package.

In this embodiment, VRX/40 Faxcard with VoiceView firmware works in the background of a telephone call. When the VRX/40 Faxcard senses data, the VRX/40 Faxcard mutes the handset of the phone connected through the VRX/40 Faxcard and begins data reception. Once the data is received, the VRX/40 Faxcard reactivates the handset and resumes the role of passive listener. For originating data transmission, a VRX/40 Faxcard "borrows" the line from the voice conversion and mutes the handset until the transmission is finished. In short, VRX/40 Faxcard is an "alternating" or "switched" voice/data transmission standard. A key feature of VRX/40 Faxcard is simplicity of use, requiring no special actions on the part of the user.

The benefits of this embodiment are that the doctor and patient could interact by voice and through a computer screen using this technology. There could be speech interaction and changing images, allowing multimedia capabilities.

In an embodiment, telephony circuits 105 includes, 1) a D/240SC-T1 voice card supplied by Dialogic, located at 1515 Route 10, Parsippany, N.J. 2) a Dialogic TTS/80 text-to-speech card, 3) a CP4/SC Fax card supplied by GammaLink, located at 1314 Chesapeake Terrace, Sunnyvale, Calif. 94089, 4) a Dialogic VRP connector with two Dialogic VRM/40 daughter cards for speech recognition. Connections between the Dialogic D/240SC-T1, the Dialogic TTS80 card, the GammaLink CP4/SC card and the Dialogic VRP card are by Dialogue PEB connection bus. PEB is a digital bus that transmits voice and signal information between various hardware devices in telephony circuit 105. Text-to-speech software and drivers are supplied by Berkeley Speech Technology, located at 2246 Sixth Street, Berkeley, Calif. and GammaLink fax drives are stored in RAM 109. Dialogic drivers and VOS™ software and drivers are likewise stored in RAM 109. In this embodiment, 24 lines may be accessed simultaneously through digital T1 interface.

In another embodiment, telephony circuits 105 include a Dialogic D/121B voice card, a Dialogic LSI/120 12-port stand alone telephone network interface, and a Dialogic SA 120 cable that attaches to the back of the Dialogic LSI/120 interface and provides phone jacks for attaching analog lines. In this embodiment, 12 analog lines may be accessed simultaneously.

Display 111 and Keyboard 112 allow access to system 100 by way of processor 107. Remote laboratory information may be obtained from a server 104 and input/output interface 113. Laboratories may enter laboratory results directly to disc 106 by way of server 104 and I/O interface 113. For example, server 104 receives data by way of either internet access 114a, computer 114b, electronic mail 114c or modem 114d.

Figure 2:
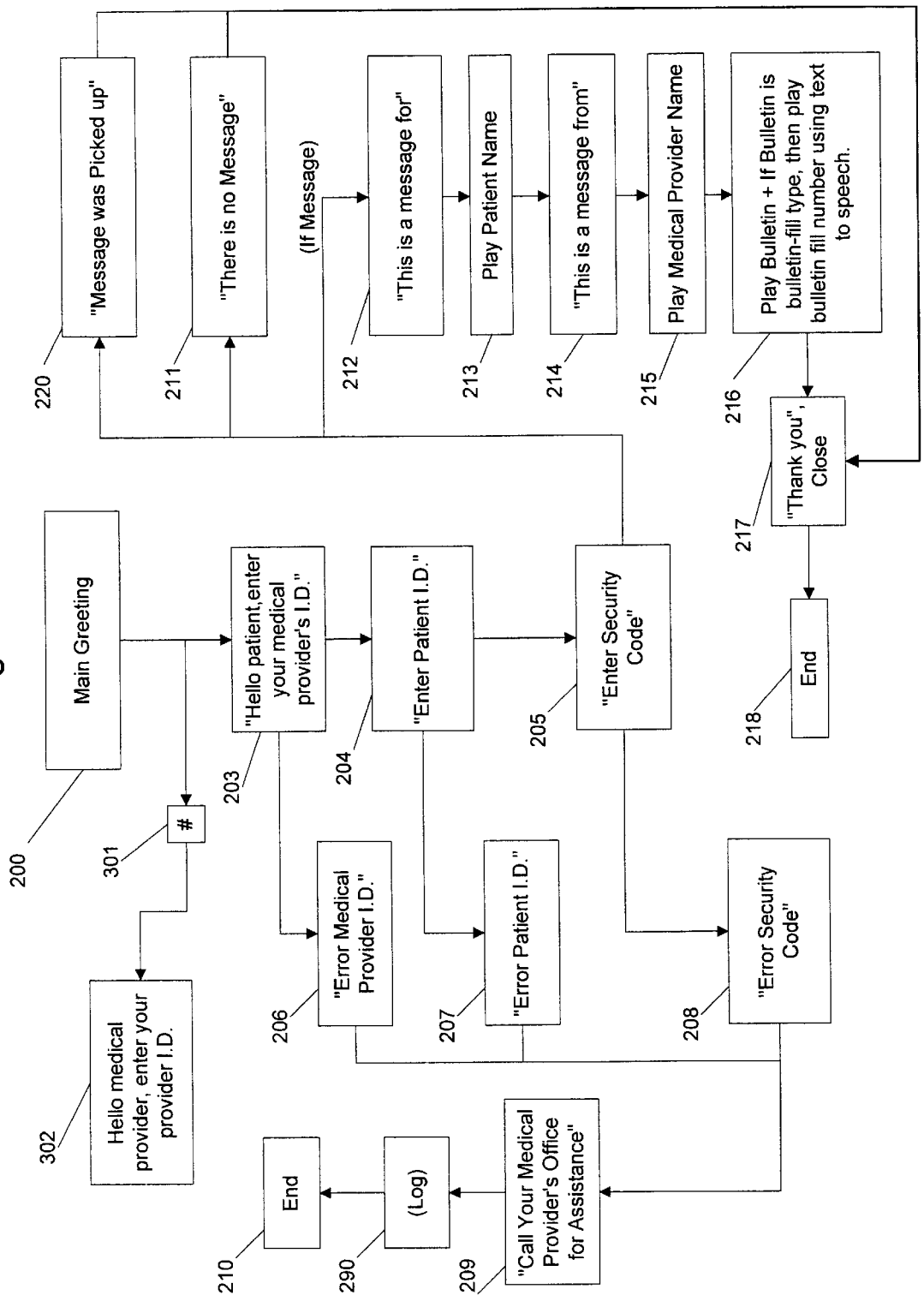
FIG. 2 illustrates a logic flow diagram of a patient receiving a medical message, in the automated patient information retrieval system, according to the present invention.

FIG. 2 illustrates a logic flow diagram of a patient obtaining a bulletin or medical message on system 100 in FIG. 1. For example, a patient may contact system 100 on telephone 101a. A medical provider likewise may access system 100 to access information or creating bulletins. While the present invention is described by using a touchtone telephone for inputting information, it should be understood that pulses, as well as voice and electronic files or data, may be input by a user to access, record, and control information in system 100.

At any level or prompt during accessing system 100, a user, such as a medical provider or patient, may enter "*" on a touchtone telephone in order to receive a help message associated with that level or prompt. Likewise, a user may enter a "#" on a touchtone telephone in order to replay a previous message prompt or to move backward one menu. At certain times, a user, in particular a medical provider, may enter "#" to access medical provider menus. A user does not have to wait for a prompt to end and may enter a sequence of inputs or touchtone pulses. In an embodiment, inputs are stored in a buffer saving a sequence of inputs.

A main greeting is generated at logic block 200 after a user telephones system 100. Processor 107 will access main greeting message from disc 106 and generate a greeting message.

In an embodiment, voice prompts are prerecorded speech. For example, studio recorded speech or telephone speech is fed through the voice processing circuit 105a. The voice processing circuit samples the analog speech 129,000 times per second to form a digital wave pattern. This pattern is then compressed to 24,000 to 32,000 samples per second and stored in disk 106. Playing a prompt is the reverse of this process. However, speech files are played at the compressed rate.

As with other messages described herein, processor 107 will access the appropriate prompt or voice mailbox message from disc 106. The main greeting 200 will prompt a patient to enter a medical provider identification ("ID") number in logic block 203.

In an embodiment, the medical provider identification number, patient identification number, security number, and how to contact system 100 is supplied by a medical provider to a patient on a written card by a medical provider. For example, a patient may be provided with a telephone number or e-mail address.

Alternatively, a medical provider, for example, a physician, may enter the "#" sign at logic block 301, followed by the medical provider identification number in logic block 302 to access a medical provider menu.

A patient then enters a medical provider identification number and processor 107 then compares the entered medical provider ID number with a stored medical provider ID number in disc 106. If a medical provider ID is matched, an enter patient ID prompt is generated in logic block 204. Otherwise, an error message is generated in logic block 206 and a message requesting the user to call the medical provider's office for assistance is generated in logic block 209 and system 100 hangs up in logic block 210 after the event is logged in logic block 290. The present system uses multiple error messages at each level or prompts to aid in training. For example, if a user selected an inappropriate input, a first error message would be generated. If the user generated the same inappropriate input, a different error message would be generated.

An enter patient ID message is generated in logic block 204. A user then enters a patient identification number. As with the medical provider ID number, the patient ID number is also compared with a patient ID number in disc 106. If a match is made, the enter security code prompt is generated at logic block 205. Otherwise, an error patient ID message is generated in logic block 207. A message requesting the user to call the medical provider's office for assistance is generated in logic block 209 and system 100 hangs up in logic block 210 after the event is logged in logic block 290.

A user is then asked to enter a security code in logic block 205 and a user enters a security code. Likewise, system 100 compares the entered security code with a security code associated with the patient ID number and medical provider ID number. A call medical provider's office message is generated in logic block 209, and system 100 hangs up in logic block 210 after the event is logged in logic block 290 if a match does not occur after two attempts.

System 100 allows for enhanced security in delivering sensitive medical information. Both the medical provider ID and patient ID must be entered, along with the security code, before information may be accessed by a patient. Thus, a third-party may not access the information. Also, it will be unlikely that sensitive medical information will be inadvertently delivered to the wrong recipient or patient.

A determination is then made whether or not a voice message containing medical information is available or has not been received by the patient. If the message has been accessed or picked up, a message stating that the message has been obtained is generated in logic block 220. If there is no message, a message describing that no message is present is generated in logic block 211.

If a message containing medical information is available, the message is then generated in logic blocks 212–216. For example, a "this is a message for" message is generated in logic block 212. The patient's name is then played in logic block 213. A "this is a message from" is then generated in logic block 214. The medical provider's name is then generated in logic block 215. Finally, a bulletin or medical information is provided in logic block 216. As described below in detail, this bulletin or medical information may be a personal prerecorded bulletin which if contains fill numbers will be played as described below: A "thank you" message is generated in logic block 217 and system 100 hangs up in logic block 218.

Figure 3:
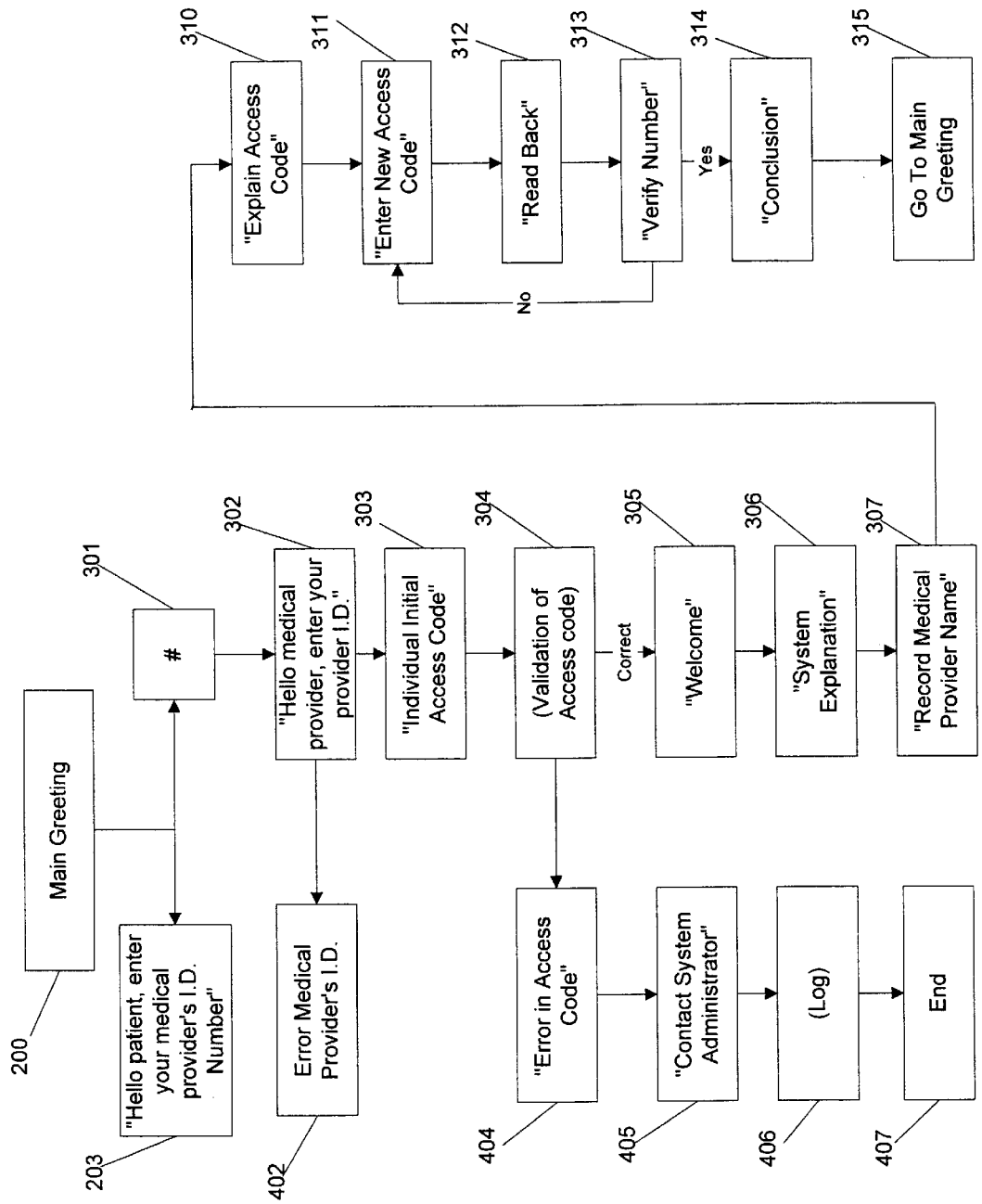
FIG. 3 illustrates a logic flow diagram of a medical provider entering the automated patient information retrieval system for the first time and recording a medical provider name and selecting a personnel access code according to the present invention.

FIG. 3 illustrates the first access of system 100 by a medical provider to install his name and personal identification access code. After listening to the main greeting in logic block 200, a "#" is entered by the medical provider from a touchtone telephone in logic block 301. The medical provider, for example, a physician, may enter a medical provider ID number in logic block 302 after listening to an enter medical provider identification number prompt followed by an individual initial access code in logic block 303. This individual initial access code is a code provided to the medical provider by the system administrator for an initial access and must be changed. System 100 then compares the medical provider ID number and individual initial access code to individual initial access codes stored on disc 106. If the medical provider does not enter the proper individual initial access code, an access code error message is generated in logic block 404, along with a contact system administrator message in logic block 405 after two attempts. The event error is then logged (message sent to system administrator) in logic block 406 and system 100 hangs up in logic block 407.

If access code is correct, a welcome message is then generated in logic block 305, followed by an explanation of operating system 100 in logic block 306. The medical provider then may record a name which will be generated in logic block 215 of FIG. 2 in logic block 307. Logic block 307 is explained in further detail in FIG. 6a. An explanation of the access codes is generated in logic block 310. The medical provider then enters a new access code in logic block 311 which supersedes the previous initial access code. The new access code is read back in logic block 312. In logic block 313, a message is generated stating that "if this is correct, press '1', if not, press '2'." If the medical provider presses "1", the message system continues, otherwise, if the medical provider presses "2", the enter access code message is generated again in logic block 311. A conclusion message is prompted in logic block 314 and the main greeting message is repeated in logic block 315.

Figure 4:
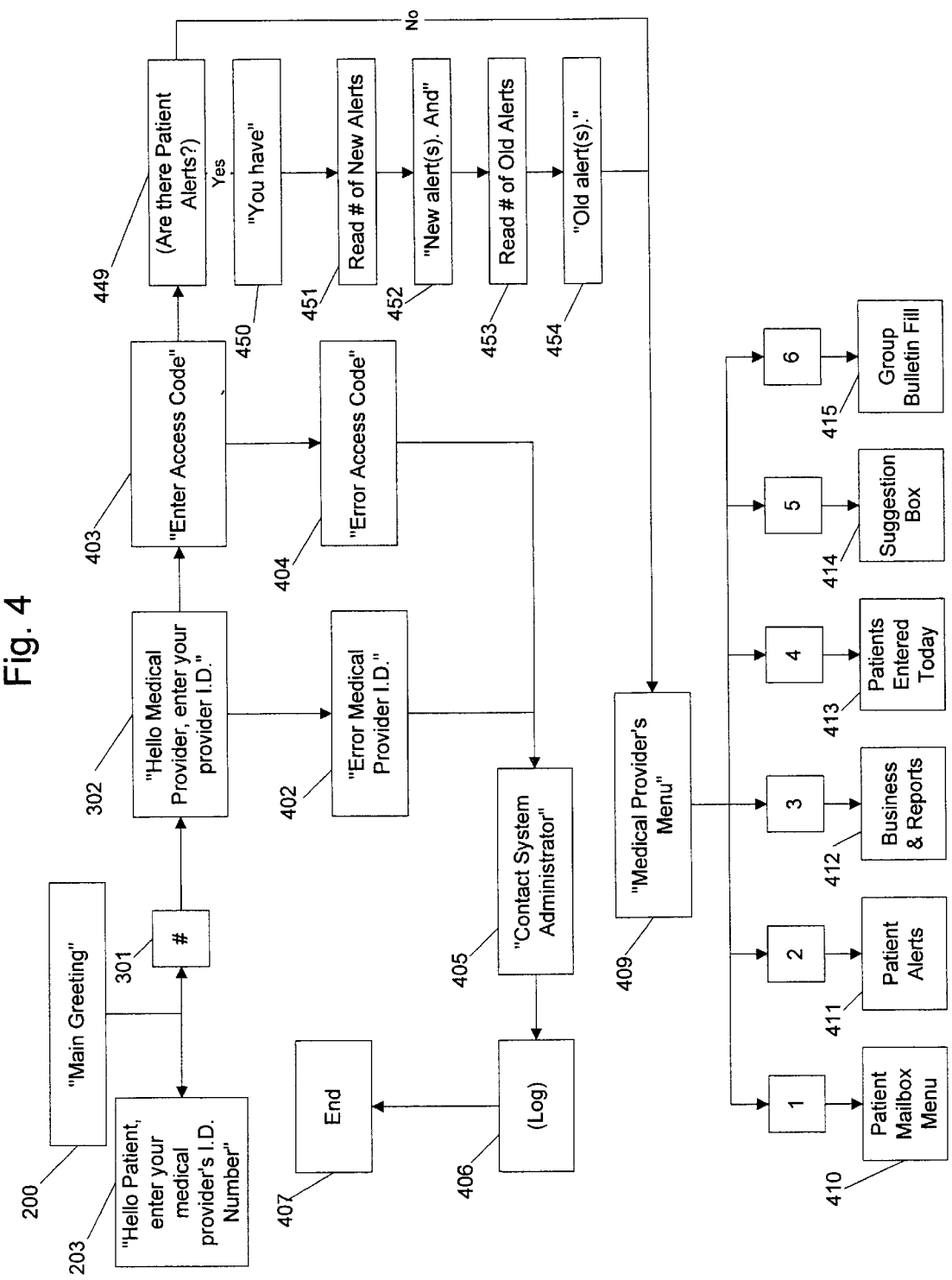
FIG. 4 illustrates a logic flow diagram of a medical provider accessing a menu in the automated patient information retrieval system according to the present invention.

FIG. 4 illustrates the medical provider main menu according to the present invention. After a greeting message is generated in logic block 200, the medical provider presses the "#" on a touchtone telephone in logic block 301. An enter medical provider's ID number prompt is generated in logic block 302. The medical provider then enters the medical provider ID number in logic block 302. System 100 then will compare the medical provider's ID number to those stored in disc 106. If the medical provider's ID number is not present, an error message is generated in logic block 402 and a contact system administrator message is generated in logic block 405 after two attempts. The error message is logged in logic block 406 and system 100 hangs up in logic block 407. If a correct medical provider's ID is provided, an enter access code message is generated in logic block 403 and an access code may be entered. Likewise, the access code is compared to existing access codes in disc 106. If the access code is correct, the number of new current patient alert messages is generated in logic blocks 450, 451, and 452 and the number of old patient alert messages is generated in logic blocks 453 and 454 if there are any patient alerts for the medical provider.

Alternatively, an error access code message is generated in logic block 404, along with a contact system administrator message in logic block 405 after two attempts. The error is then logged in logic block 406 and system 100 hangs up in logic block 407.

Logic blocks 450, 451, 452, 453, and 454 generate a message notifying a medical provider as to how many alerts are present. Logic block 450 generates a "you have" message. Logic block 451 plays the number of new alerts; logic block 452 plays a "New alert. And" message. Subsequently logic block 453 plays the number of old alerts and logic block 454 plays an "Old alert" message. The number of new patient alerts read in logic block 451 refers to the number of patients who have not received their messages in a time predetermined by a medical provider and which have not been listened to by the medical provider as yet. Once the medical provider listens to a "new alert" it is changed to an "old alert." This will be described in detail below. Old alerts may be deleted after a predetermined amount of time.

A medical provider's menu message prompt is generated in logic block 409 which provides the medical provider six alternatives by pressing numbers 1–6 on a touchtone telephone. The alternatives include a patient mailbox menu in logic block 410, patient alerts in logic block 411, business and reports in logic block 412, patients entered today in logic block 413, a suggestion box in logic box 414, and a group bulletin fill option in logic block 415.

Figure 5:
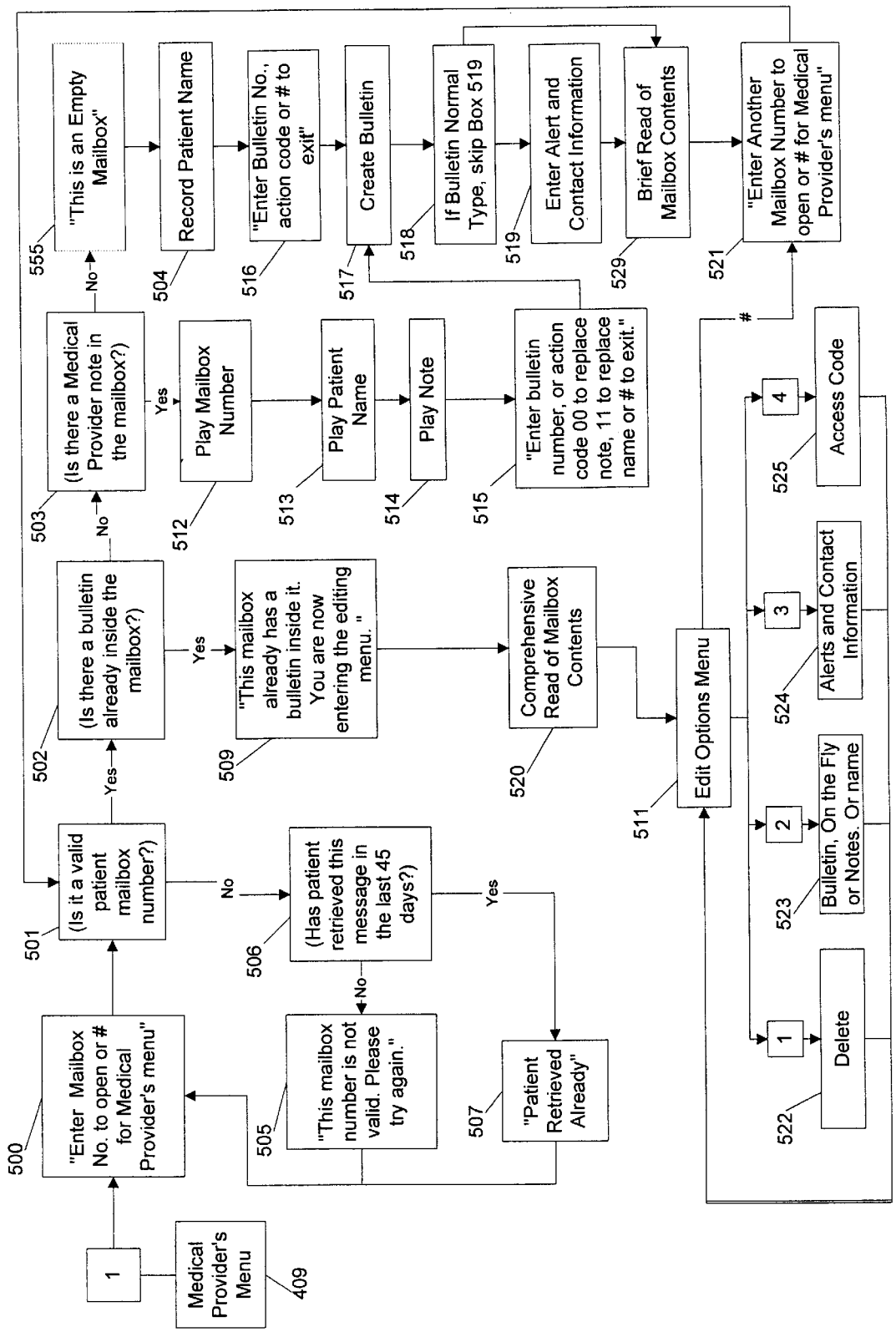
FIG. 5 illustrates a logic flow diagram of placing or editing a bulletin or a medical message for a patient in a patient mailbox in the automated patient information retrieval system according to the present invention.

FIG. 5 illustrates a logic flow diagram for creating and editing medical information in mailboxes or bulletins in disc 106. After entering a "1" at the Medical providers Menu in logic block 409 the medical provider is prompted by logic block 500 to enter a mailbox number to open. The further processing of bulletin creation or editing is dependent on the bulletin type code number. A bulletin number field associated with that bulletin is stored on disc 106. Based upon the bulletin type or code number as well as contents of mailbox opened, system 100 will automatically prompt a medical provider with the appropriate prompts. This method allows the medical provider to skip numerous redundant steps, saving valuable time.

There are several bulletin types as indicated in the following tables:

(1) System Pre-Recorded Bulletins: Examples of system prerecorded bulletins are shown in Table A below. Their bulletin numbers are coded by two digits, the first being a digit from 2 to 9 or the equivalent letter on a touch tone button so numbered and the second digit also being from 2 to 9. An example is "T1" or "81": 'Your recent test was normal.'

(2) Personal Pre-Recorded Bulletins: Information relating to bulletin numbers for these bulletins is shown in Table B. These bulletins all have identification bulletin numbers that begin with "0" and consist of three digits. Bulletins with numbers from 010 to 030 consist of only a message. For example: "Your cholesterol level is elevated so you should follow the diet suggestions I gave you in my office." Bulletins with numbers from 031 to 060 contain number fields which can be entered into personal prerecorded bulletins by the medical provider: For example, bulletin number 052 would be presented as two phrases separated by a number field: "Your fasting blood sugar", "Enter a number" (Response for example could be "102"), "Stay on the same medication dosage." These personal prerecorded bulletins can be created by the medical provider in logic box 850 in FIG. 8 and FIG. 9, which will be discussed below.

(3) 'On-the-fly' Bulletins: These bulletins are recorded by the provider on-line while the bulletin is being created. All these bulletins have "99" as their bulletin numbers.

(4) Medical Provider Notes: These are messages or notes entered into a specific patient mailbox by a medical provider which are only accessible by a medical provider or authorized individual. All these bulletins have "00" as their bulletin numbers in the number field associated with the bulletin and stored on disc 106.

Also, the medical provider has action codes which may be entered at the "enter bulletin code prompt." These action codes, listed in Table C, allow the medical provider to record the patient's name, record a medical provider note, record an on the fly message, or to have system 100 send a fax to the medical provider of the bulletin and action codes available.

TABLE A

| Bulletin Number | System Pre-recorded Messages or Bulletins |
| --- | --- |
| T1 | Your recent test was normal. |
| T2 | Your recent test was not normal; please call the office. |
| T3 | Your recent test was not normal. Stay on your medication. |
| P1 | Your Pap Smear was negative. |
| P2 | Your Pap Smear shows need for follow up; please call the office. |
| L1 | Your Strep test was negative. |
| L2 | Your Strep test was positive; please call the office. |
| L3 | Your Strep test was positive; stay on medication. |
| M1 | Your mammogram is normal |
| M2 | Your mammogram shows need for further follow up; please call the office. |
| X1 | Your X-ray test was normal. |
| X2 | Your X-ray test needs follow-up; call the office. |
| G1 | Your pregnancy test was negative. |
| G2 | Your pregnancy was positive; call for instructions. |
| C1 | Your cholesterol level is ###. |
| C2 | Your cholesterol level is ###. Please call for appointment. |
| 1P1 | Your PSA test is normal. |
| 1P2 | Your PSA test was ## point #. |
| 1G1 | Your blood sugar is ###. or (##) |
| 1G2 | Your blood sugar is ###, or (##). Please call for instructions. |
| A1 | Your urine test was normal. |

TABLE A-continued

| Bulletin Number | System Pre-recorded Messages or Bulletins |
|---|---|
| A2 | Your urine test was not normal; please call the office. |
| A3 | Your urine test shows an infection; stay on your medication. |
| A4 | Your urine test shows an infection; your medication needs to be changed. |
| E1 | Your thyroid tests are normal. |
| E2 | Your thyroid tests are normal; stay on your current dose of medication. |
| E3 | Your thyroid tests show needs to adjust your medications; please call. |
| H6 | Your hemoglobin A1c test is # point #. This is good control. |

TABLE B

| Bulletin Number | System Pre-recorded Messages or Bulletins |
|---|---|
| 010–030 | Just Message |
| 031–035 | [Message] + [Number ### No Point] |
| 035–040 | [Messaqe] + [Number ### Point #] |
| 041–045 | [Number ### No Point] + Message |
| 046–050 | [Number ### Point #] + Message |
| 051–055 | [Beginning Message Segment] + [Number ### No Point] + End Message Segment] |
| 055–060 | [Beginning Message Segment] + [Number ### Point #] + End Message Segment] |

| Action Code | Action Type |
|---|---|
| 11 | Record Name |
| 00 | Record Medical Provider Note |
| 99 | Record On the Fly Message |
| FAX (329) | Send Fax of Bulletin Codes |

Subsequent to logic block 500, system 100 next determines if the entered patient mailbox number is valid in logic block 501. If the mailbox number is not valid, a determination is made in logic block 506 to ascertain if the patient has retrieved a bulletin from this mailbox in a prior selected time period, such as 45 days. System 100 prevents further access to mailboxes for editing after the bulletin is accessed by the patient. If this is the case, logic block 507 informs the medical provider and returns to logic block 500. If an error in entry of the mailbox number was made, logic block 505 so informs a medical provider and returns to logic block 500.

If a valid patient mailbox number was entered, system 100 determines if there is a bulletin already stored in the selected mailbox in logic block 502. If system 100 determines that a bulletin has been stored, a medical provider is switched to an edit options menu in logic block 511 after being informed of this by logic block 509 and having the full contents of mailbox read by logic block 520. Logic block 520 is described in more detail below and illustrated in FIG. 6c. From the Edit Options Menu in logic block 511, a medical provider may either choose several sub-menus to be discussed below for modifying the mailbox number or contents A "#" may be entered to jump to logic block 521.

If logic block 502 determines that there is no bulletin stored in the mailbox, logic block 503 next ascertains if there is a medical provider note associated with the mailbox. If a medical provider note exists in the mailbox, system 100 plays the mailbox number in logic block 512, the patient's name in logic block 513, and the medical provider note in logic block 514. The medical provider is then prompted by logic block 515 to either enter a bulletin code number, "00" to replace the medical provider note, "11" to replace the patient's name, or "#" to exit to the Medical providers Menu. The medical provider is then advanced to the create bulletin logic block 517, which is described in detail below and illustrated in FIG. 6b.

If in logic block 503 system 100 determines that a medical provider note is not associated with the mailbox, an empty mailbox received prompt is generated in logic block 555. The medical provider is then prompted to record the patient's name in logic block 504. The recording of the patient name is discussed in detail below and illustrated in FIG. 6a. A bulletin number or "#" to exit is entered in logic block 516. If a bulletin number is entered, logic block 517 creates the bulletin as illustrated in FIG. 6b. If the bulletin is one giving normal results, logic block 518 advances the medical provider to logic block 529 where a "brief" reading of mailbox contents is performed as described below and illustrated in FIG. 6c. If the bulletin is not of this type, the medical provider is given the option by logic block 519 to enter information for automatic alerting and patient contacting prior to the reading of the contents of the bulletin in logic block 529. The medical provider is then prompted by logic block 521 to either enter another mailbox number and begin again at logic block 501 to open another mailbox or to enter "#" to exit to the medical provider's menu.

Figure 6A:
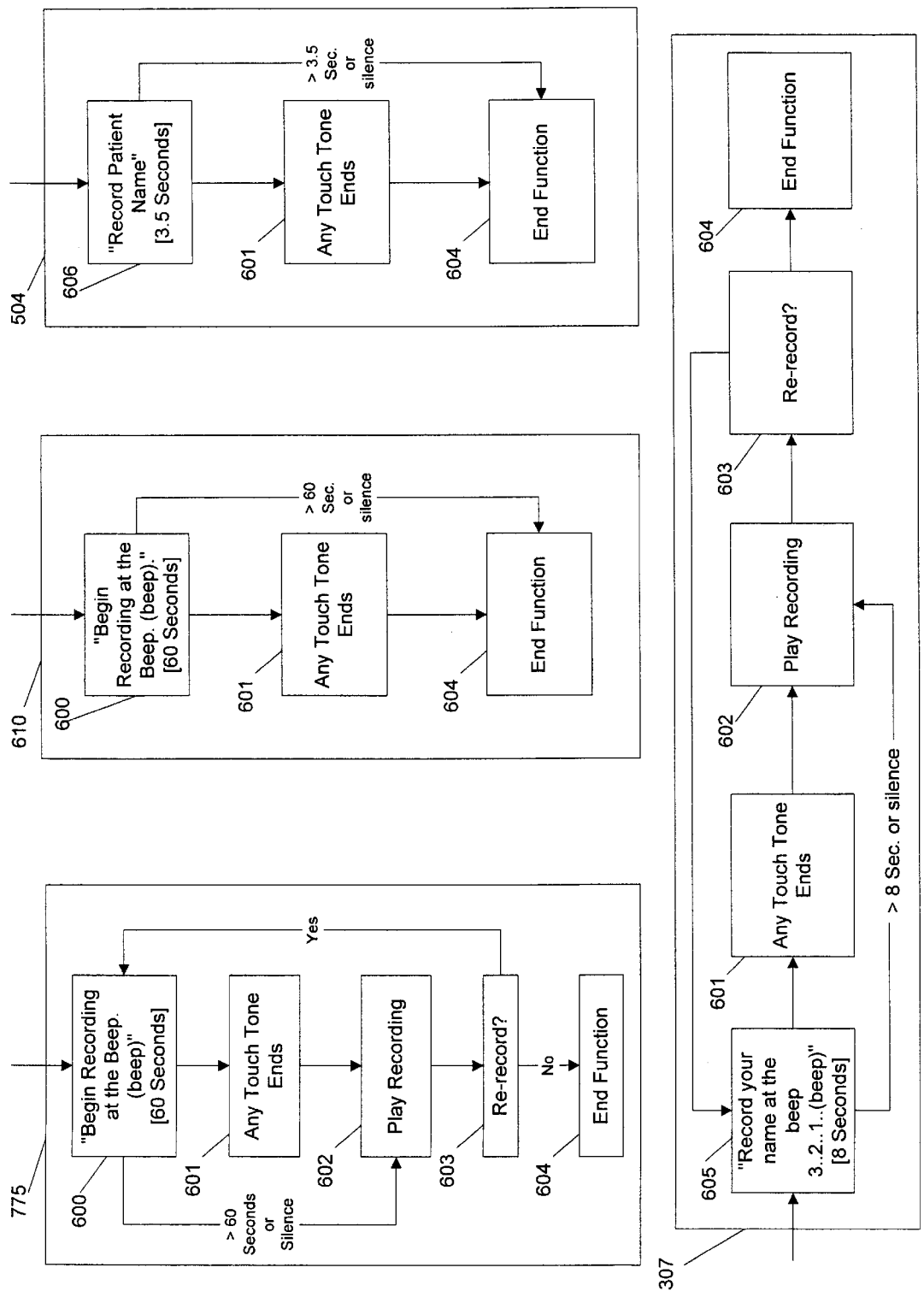
FIG. 6a–f illustrate a logic flow diagram of a) several recording information paradigms; b) creating a bulletin, recording messages, and recording notes; c) repeating patient information (logic block 750), 'Comprehensive Read' of mailbox contents (logic block 520), 'Brief Read' of mailbox contents (logic block 529), and faxing a list of bulletin code numbers and their descriptions (logic block 698); d) setting alerts and contacting information for patients; e) contacting patients; and f) playing patient alert and contact information (logic block 630) and detailed flow diagrams of the four choices in the Edit Options Menu (logic blocks 522, 523, 524, and 525); in the automated patient information retrieval system according to the present invention, respectively.
Figure 6B:
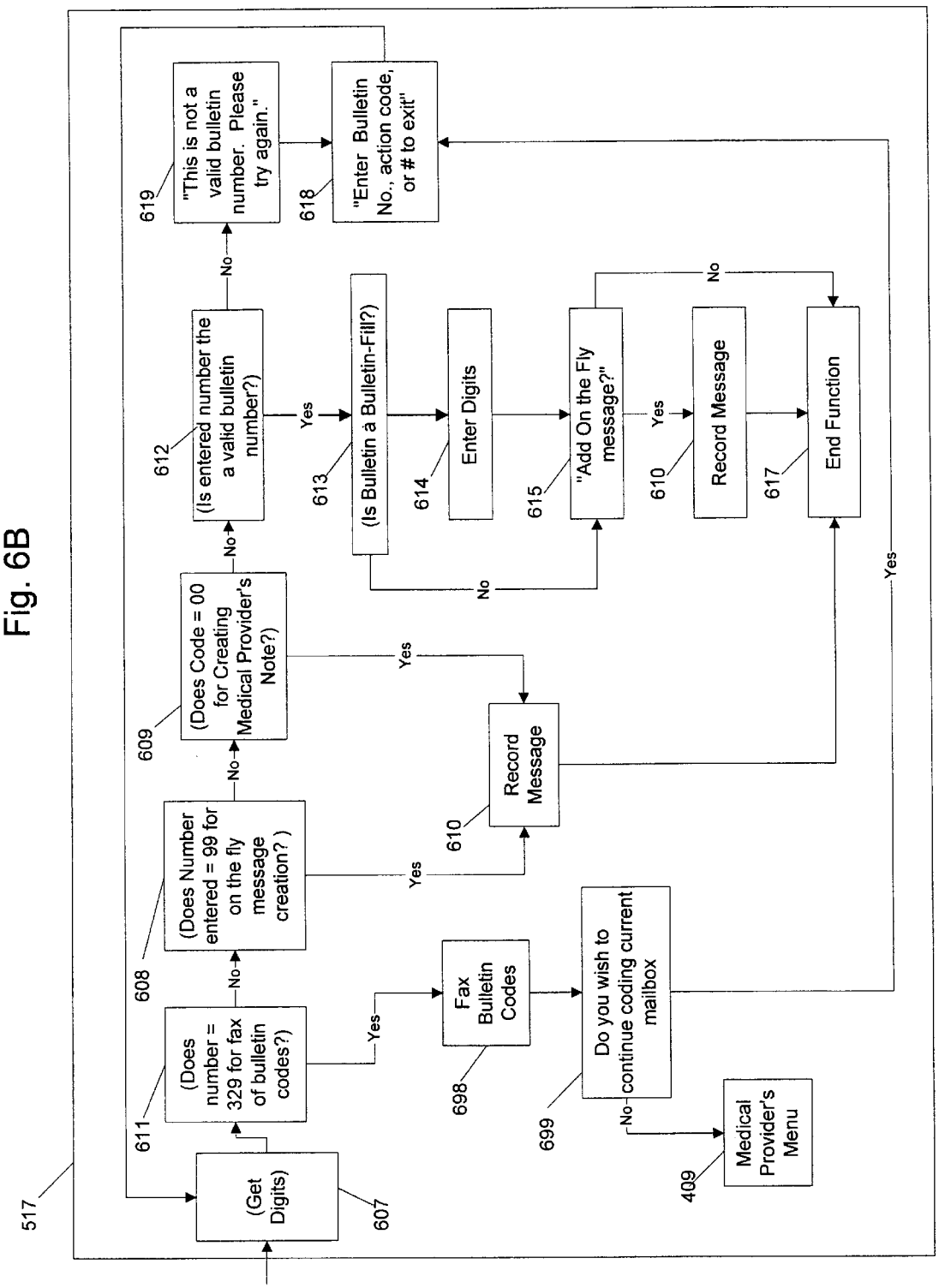

FIG. 6a illustrates different logic flow diagrams for recording information on-line: In logic block 775, a user is first prompted by logic block 600 to begin recording at the 'beep'. A 'beep' is then played and a recording that may last up to 60 seconds is begun. Any touch tone input, or silence lasting a predetermined length, ends the recording as per logic block 601. The recording is then played by logic block 602 and an option to re-record or end the function is given in logic block 603. The function ends in logic block 604.

In logic block 610, logic block 600 prompts a user to begin the recording at the 'beep'. After a beep, 60 seconds of recording time is available. A silent period of a predetermined length or any touchtone input ends the recording as per logic block 604.

In logic block 504, entering a "Name" is prompted and must be entered within a specified time period, such as a 3.5 second duration in logic block 606. Logic block 604 ends the function either after the entry of any touch tone in logic block 601 or if the recording exceeds 3.5 seconds or a silence of a predetermined length.

In logic block 307 a recording prompt consisting of "Record you name at the beep 3. . . 2. . . 1. . . (beep)" is played and the function is ended by logic block 604 either by 1) entering any touch tone in logic block 601 2) recording for more than 8 seconds or 3) silence of a predetermined length. After the name is recorded in logic block 605, logic block 602 allows the recording to be played and logic block 603 prompts the user regarding whether or not the name should be re-recorded. If a user desires to re-record the name, control is transferred back to logic block 605; otherwise, the function ends in logic block 604.

Figure 6C:
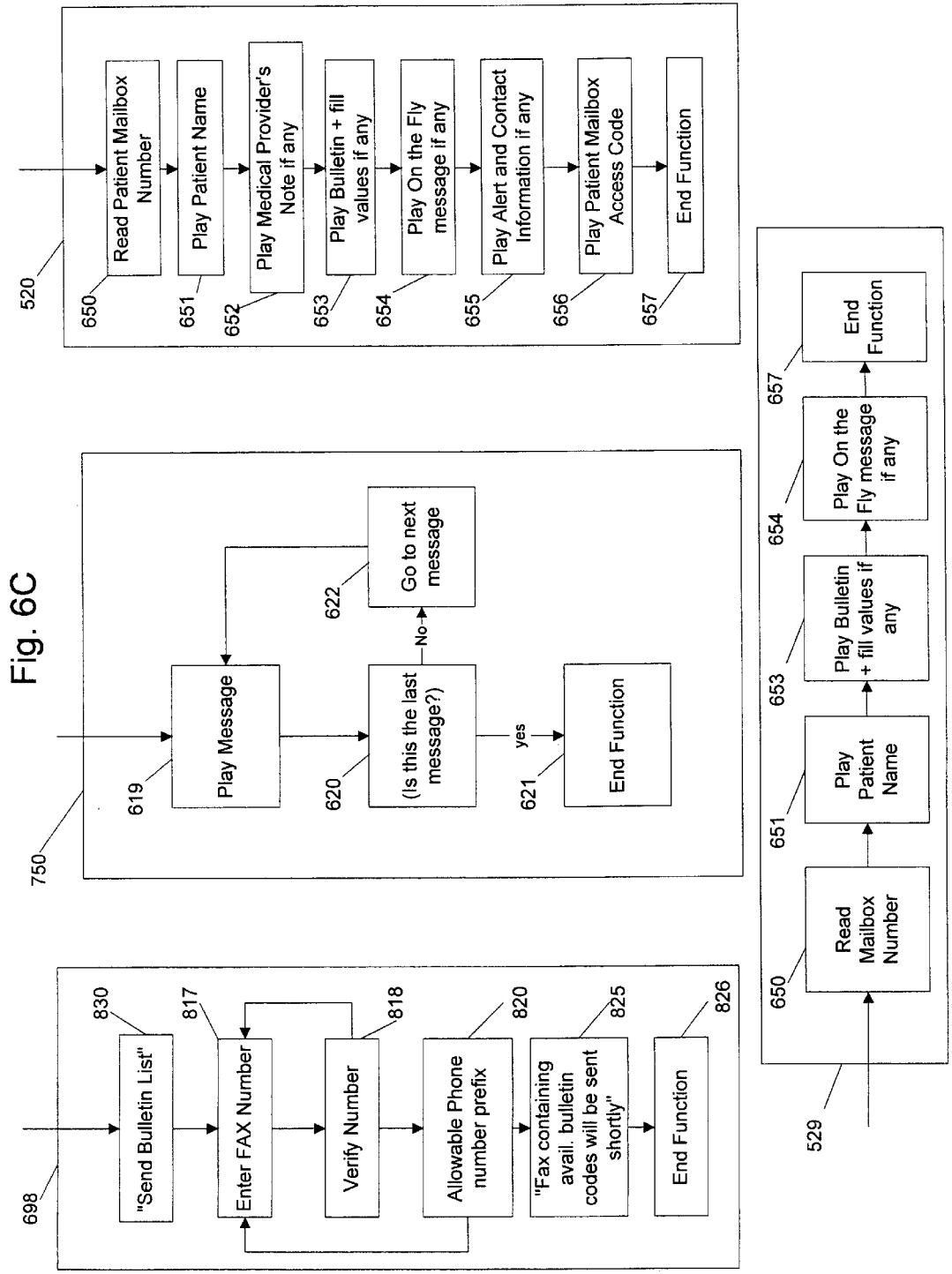

FIG. 6b illustrates creating bulletins in logic block 517. In logic block 607, system 100 reads inputs entered by a user to obtain the bulletin code or action code. The user may obtain a faxed list of bulletin codes by entering touch tone action code: "F", "A", "X" or "3", "2", "9". Logic block 611 detects if this sequence has been entered and if so logic block 698 causes a fax, including bulletin codes, to be sent, as illustrated in FIG. 6c. Logic block 699 then asks if the user wishes to continue coding the current mailbox or exit to the medical provider's menu in logic block 409. If logic block 611 determines that a user does not want a fax, logic block 608 determines if the number entered is '99' for an on-the-fly type of message and logic block 609 determines if '00' has been input to see if a medical provider note is to be created. If either one of these is the case, the bulletin message is recorded by logic block 610 and the function ends in logic block 617. If neither of these is the case, logic block 612 determines if the number entered is a valid bulletin number. If valid bulletin number is not entered, logic block 617 informs the user that a valid bulletin number has not been entered and in logic block 618 another bulletin number or action code is entered and control is transferred to logic block 607, or a "#" is entered to exit. If logic block 612 determines that the bulletin number is valid, logic block 613 determines if the bulletin is a type that requires fill-in numbers and if so these are entered in logic block 614. If the bulletin is not required to fill in numbers, system 100 jumps directly to logic block 615 where the user is prompted as to whether or not an on-the-fly type message is to be added. If not, logic block 617 ends the function. If so, logic block 610 allows recording of the on-the-fly message prior to ending.

FIG. 6c illustrates logic blocks for several different functions. Logic block 698 is used to fax a summary of bulletin codes and messages requested by a medical provider. Logic block 830 announces that the user has requested a fax containing bulletin codes to be sent. The fax number is entered in logic block 817 and verified by logic block 818. If an error is detected, control is returned to logic block 817 for re-entry; otherwise, logic block 820 next determines whether the fax phone number has a prefix that is on a predetermined list in system 100. Logic block 825 announces to the user that the fax containing bulletin codes will be sent shortly and logical block 826 ends the function.

Logic block 750 is a repeat function that plays relevant fields of one or a series of bulletins. The message is played in logic block 619. Logic block 620 determines if the last message has been accessed. If not, logic block 622 accesses the next message to be played in logic block 619. If it is the last message, logic block 621 ends the function.

Logic block 520 provides a "comprehensive" or full reading of mailbox contents. Logic block 650 first reads the mailbox number; then logic block 651 plays the patient name and logic block 652 plays any medical provider note that is present. Next the bulletin and any fill-in numbers is played by logic block 653 followed by the playing of any on-the-fly messages by logical block 654. Patient alert and contact information is then played by logic block 655 and then the patient mailbox access code is played by logic block 656 before the function ends in logic block 657.

Logic block 529 provides a "brief reading" of mailbox contents. The mailbox number is read in logic block 650 followed by the reading of the patient's name in logic block 651. The bulletin and any fill-in numbers is next played in logic block 653 and then any on-the-fly messages are played in logic block 654 before the function ends in logic block 657.

Figure 6D:
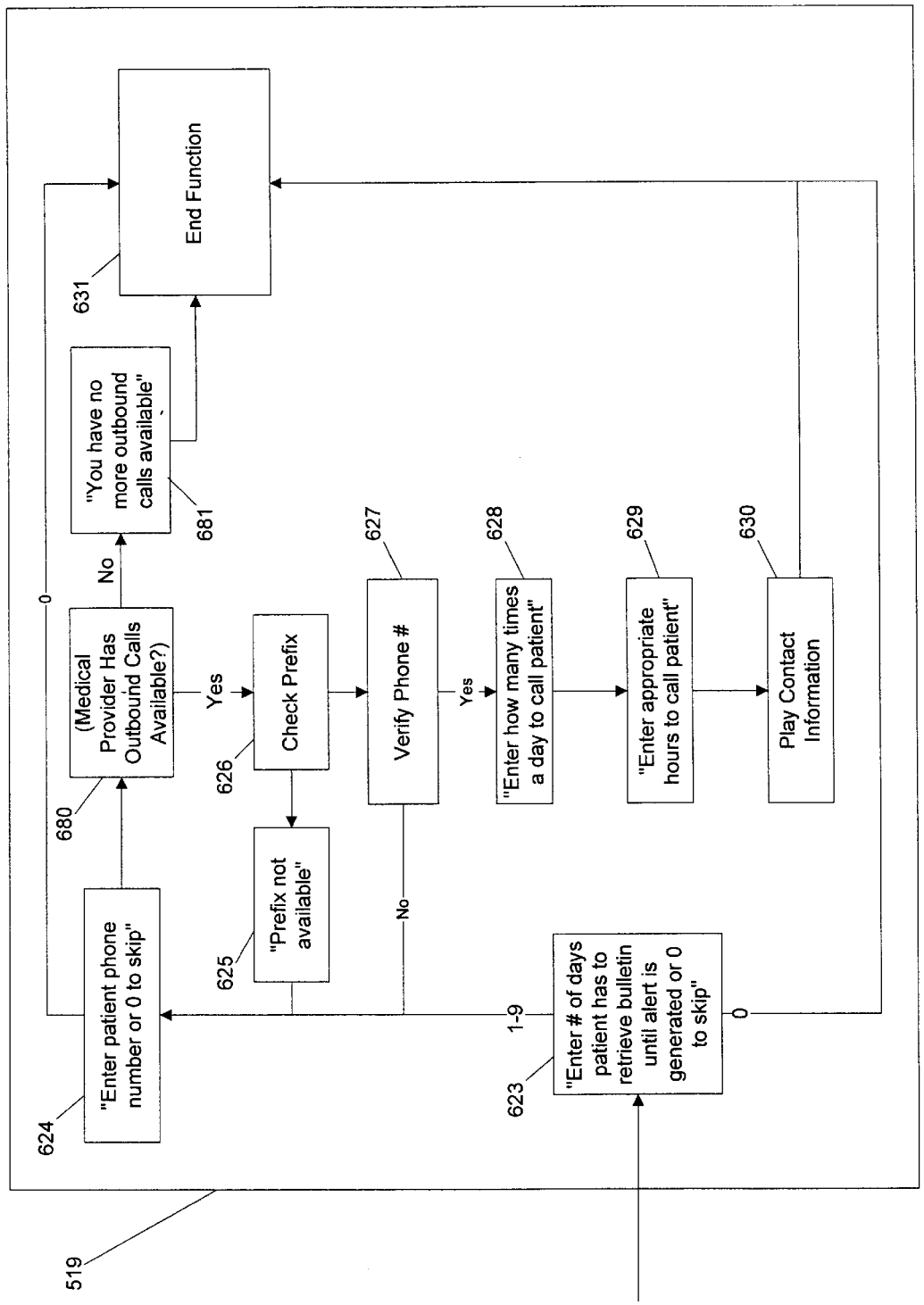

Logic block 519 in FIG. 6d illustrates entering patient alert and contact information. The number of days a patient has to retrieve their bulletin until an alert is generated is entered in logic block 623. If the medical provider enters a 0 here, the function is ended in logic block 631. If the medical provider enters a numeric digit 1 through 9, then logic block 624 prompts the medical provider to enter a phone number for system 100 to call to inform the patient that there is a waiting message from a medical provider. If the medical provider enters a 0, then the function is terminated in logic block 631. If the provider enters a phone number, logic block 680 determines whether or not the medical provider has outbound calls available. If the medical provider does not have outbound calls available, logic block 681 announces that the medical provider doesn't have any outbound calls available and the function ends in logic block 631. If the medical provider does have outbound calls available, then logic block 626 checks to see if the prefix is acceptable for system 100 to dial. If the prefix entered is not acceptable, then the system informs medical provider in logic block 625 and jumps to logic block 624 and prompts the medical provider to enter the patient phone number or 0 to skip. If logic block 626 determines that the prefix entered is acceptable, the telephone number is verified to the medical provider. The number of times to call a patient a day is entered in logic block 628. The appropriate hours to call is entered in logic block 629 and the patient alert and contact information is played in logic block 630 before the function is ended by logic block 631.

Figure 6E:
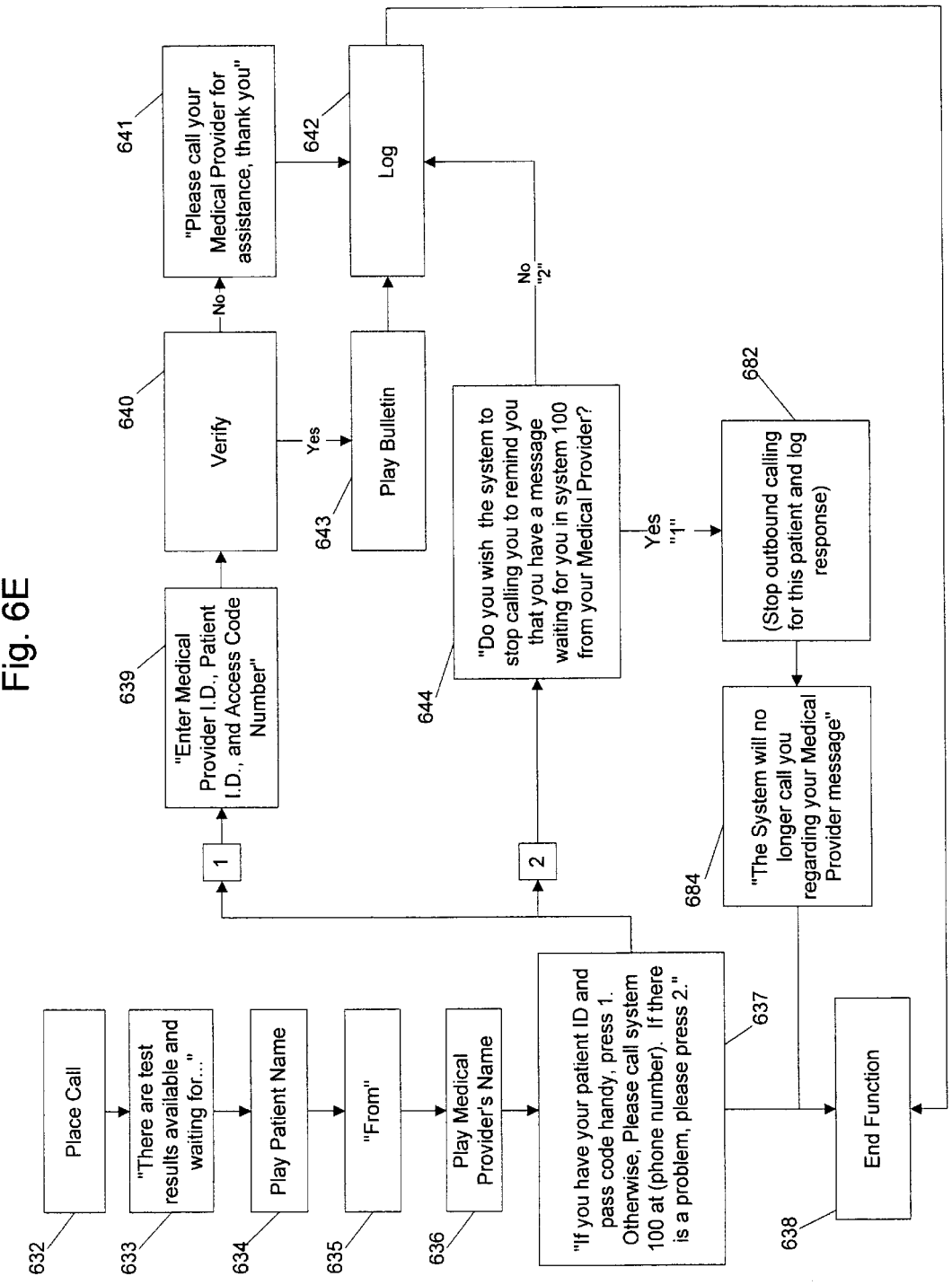

FIG. 6e illustrates a logic flow diagram for telephoning a patient. System 100 telephones in logic block 632 the patient using the information supplied as shown in FIG. 6d in logic block 624. A "There are test results and waiting for" message is then generated in logic block 633 and the patient's name is next played in logic block 634, followed by the message "from" generated in logic block 635 and the playing of the medical provider's name in logic block 636. Logic block 637 provides the patient an opportunity to enter the patient ID and passcode by pressing "1" or to call system 100 at a provided phone number. If there is a problem, the person receiving the call may press "2" and logic block 644 will prompt to press "1" if they wish for system 100 to no longer call them, or "12" to end the call. If they press "12", the event is logged in logic block 642 and the function ends in logic block 638; if a patient presses "1", system 100 stops future outbound calling to this phone number in logic block 682 and announces that system 100 will no longer call this phone number in logic block 684 before ending the function. These events are logged and the function is ended in logic block 638. If "1" is entered, logic block 639 enables the doctor ID, patient ID and code number to be entered followed by verification of these numbers in logic block 640. If the verification is successful, the bulletin is played in logic block 643 and these events logged in logic block 642 before the function is ended in logic block 638. If the verification is not successful, 641 plays a request to call the medical provider for assistance and logic block 642 logs the information before the function is ended in logic block 638.

Similarly, a medical provider could be contacted to play a note or provide a reminder.

Figure 6F:
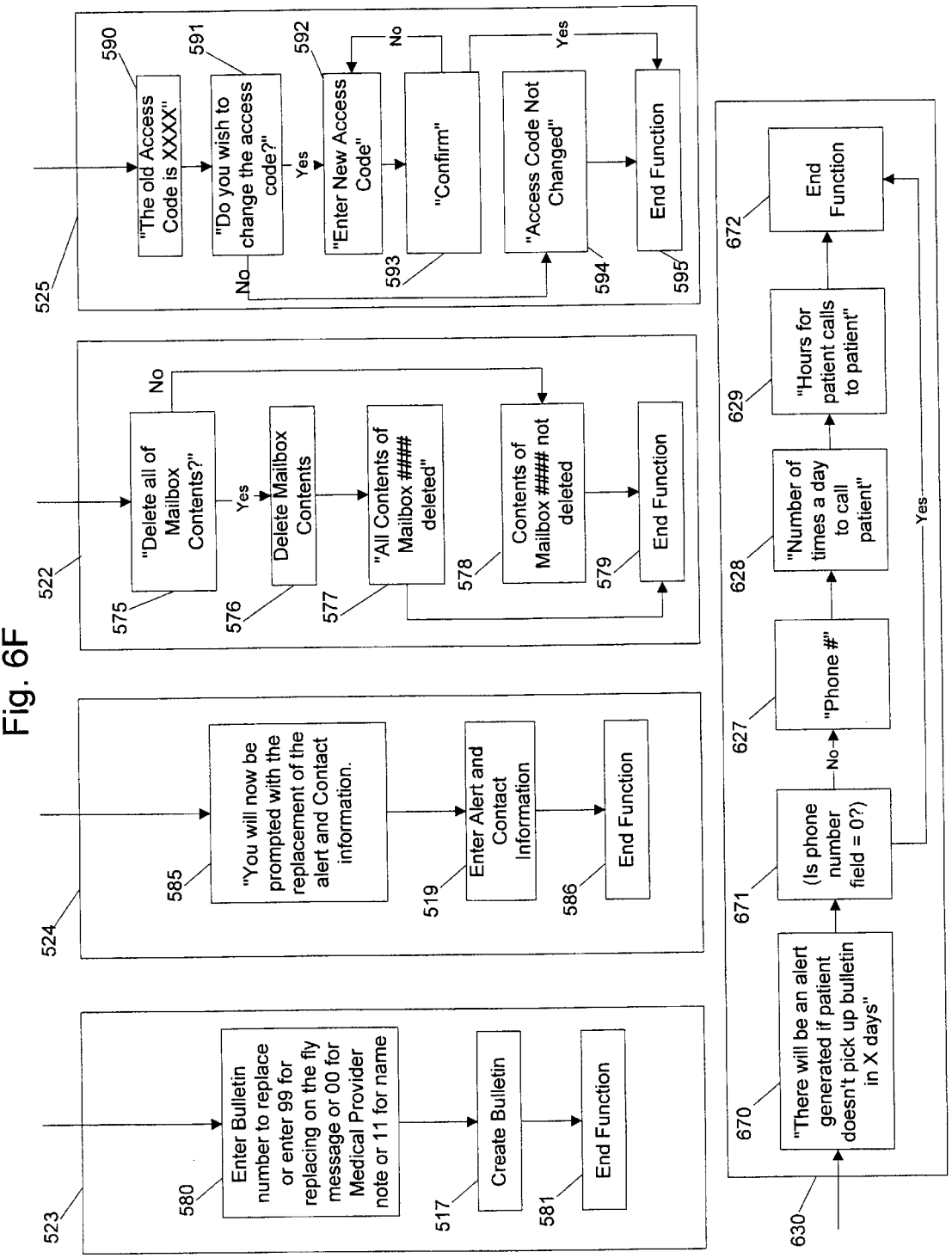

FIG. 6f illustrates logic flow diagrams for several sub-menus of the edit options menu block 511 in FIG. 5. and play patient alert & contact information logic block 630.

Logic block 523 allows editing of personal pre-recorded bulletins, on-the-fly bulletins, medical provider notes, or patient's names which are stored in mailboxes. Logic block 580 first plays a message to enter a bulletin number to replace or "99" to replace an on-the-fly-message or "00" to replace a medical provider note or "11" to replace a name. Then the new bulletin is created in logic block 517 before the function ends in logic block 581.

Logic block 524 illustrates the logic flow diagrams for replacing or updating information for contacting and alerting a patient by system 100. First, an announcement is made in logic block 585 telling the user that alert and contact information will be replaced. Then the alert and contact information is collected in logic block 519 before the function ends in logic block 586.

Logic block 522 allows deletion of all the contents of a bulletin in a mailbox. A message asking if it is desired to delete all the contents of a specific mailbox is prompted in logic block 575. If a negative reply is obtained, logic block 578 plays a message indicating the contents of the mailbox were not deleted before logic block 579 ends the function. If an affirmative answer is obtained, logic block 577 plays a message confirming the deletion of the contents of the mailbox before the function ends in logic block 579.

Logic block 525 allows for changing of the patient's access code. A message indicating the current access code is generated in logic block 590 followed by a message asking if a user wishes to change an access code in logic block 591. A negative reply results in a message that the code was not changed generated in logic block 594 before the function ends in logic block 595. A positive reply results in a new access code being entered in logic block 592; this is confirmed in logic block 593 and, if correct, logic block 595 ends the function. If there is an error the user is requested again by logic block 592 to enter a new access code.

Logic block 630 allows for playing the patient alert and contact information needed in logic block 519 for outgoing calls to patients. Logic block 670 prompts that there will be a patient alert generated if the patient does not pick up the bulletin within a predetermined period of time. Next logic block 671 ascertains if there is a phone number present in the patient's phone number field. If not, control is transferred to logic block 672 and the function ends. S Otherwise logic block 627 ascertains the patient's phone number. In logic block 628, the number of times a day the patient is to be called is played; in logic block 629, the hours during which these calls are to be made are played. Finally, logic block 672 ends the function.

Figure 7:
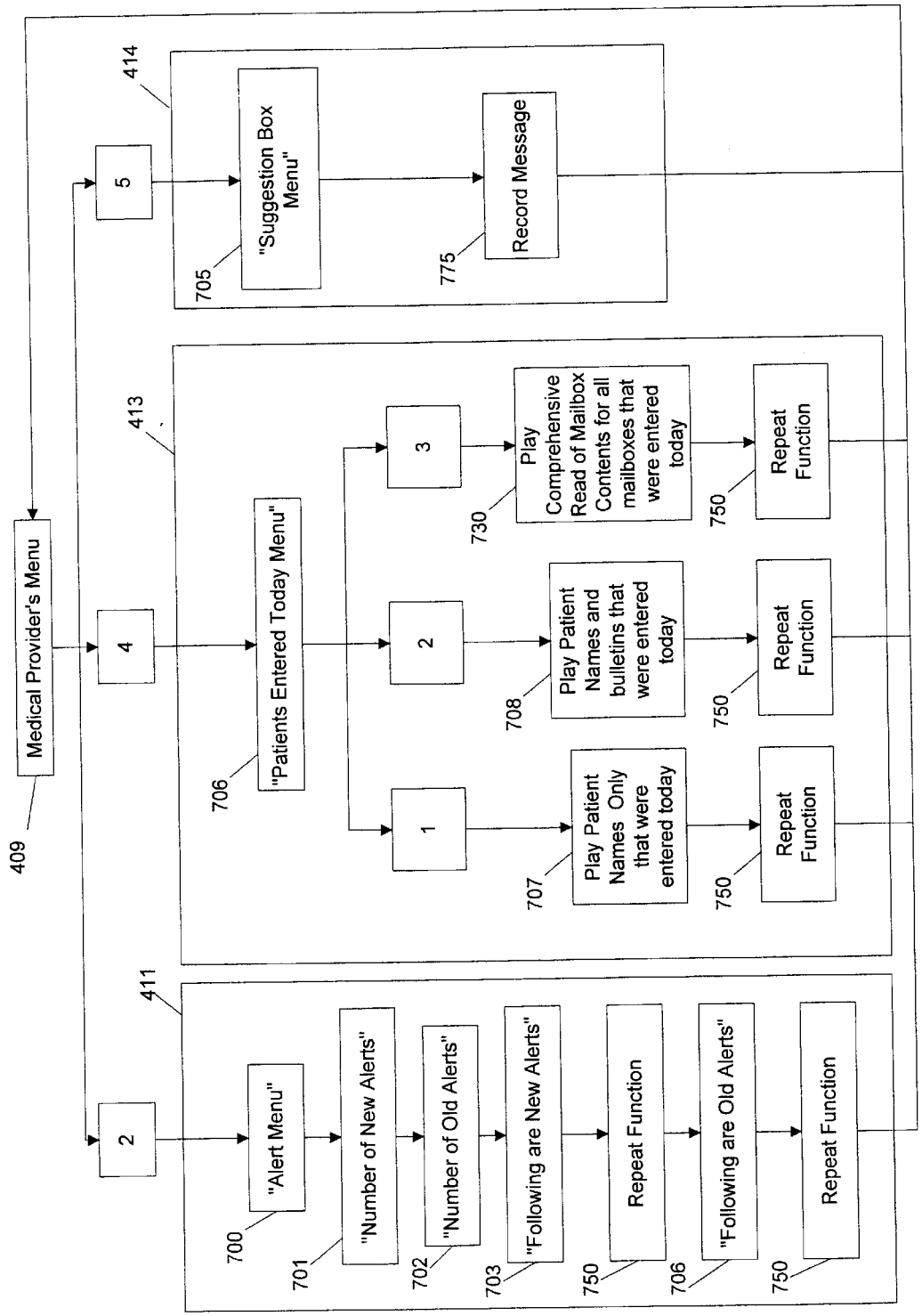
FIG. 7 illustrates a logic flow diagram of a) providing patient information alerts (logic block 411); b) playing information on mailboxes entered on the current day (logic block 413); c) entering a message in a suggestion box (logic block 414); in an automated patient information retrieval system according to the present invention.

FIG. 7 illustrates the logic flow diagrams of alerts logic block 411, patients entered today logic block 413, and suggestion box logic block 414 illustrated in FIG. 4. If a medical provider selects "2", an alert menu is announced in logic block 700 and the number of new alerts is determined in logic block 701 and the number of old alerts is determined in logic block 702. Once a medical provider listens to a bulletin, an associated bulletin status data field is altered to identify the bulletin as being an old alert. A message announcing "The following are New Alerts" is generated by logic block 703 and the new alerts are played by the repeat function in logic block 750. A message stating "the following are old alerts" is next generated by logic block 706 followed by the playing of the old alerts in logic block 750.

If a medical provider selects "4", a patients entered today menu is announced in logic block 706. Selecting "1" plays only patient names that were entered today in logic block 707. Selecting "2" plays both patient names entered today and bulletin titles and fill-in numbers in logic block 708. Selecting "3" plays comprehensive reading of the mailbox contents that were entered today in logic block 730. Logic blocks 707,730, and 708 are followed by the repeat function in logic block 750.

A suggestion box introduction message is generated in logic block 705 after a medical provider selects "5". After a suggestion box prompt, a message can be recorded in logic block 775.

Figure 8:
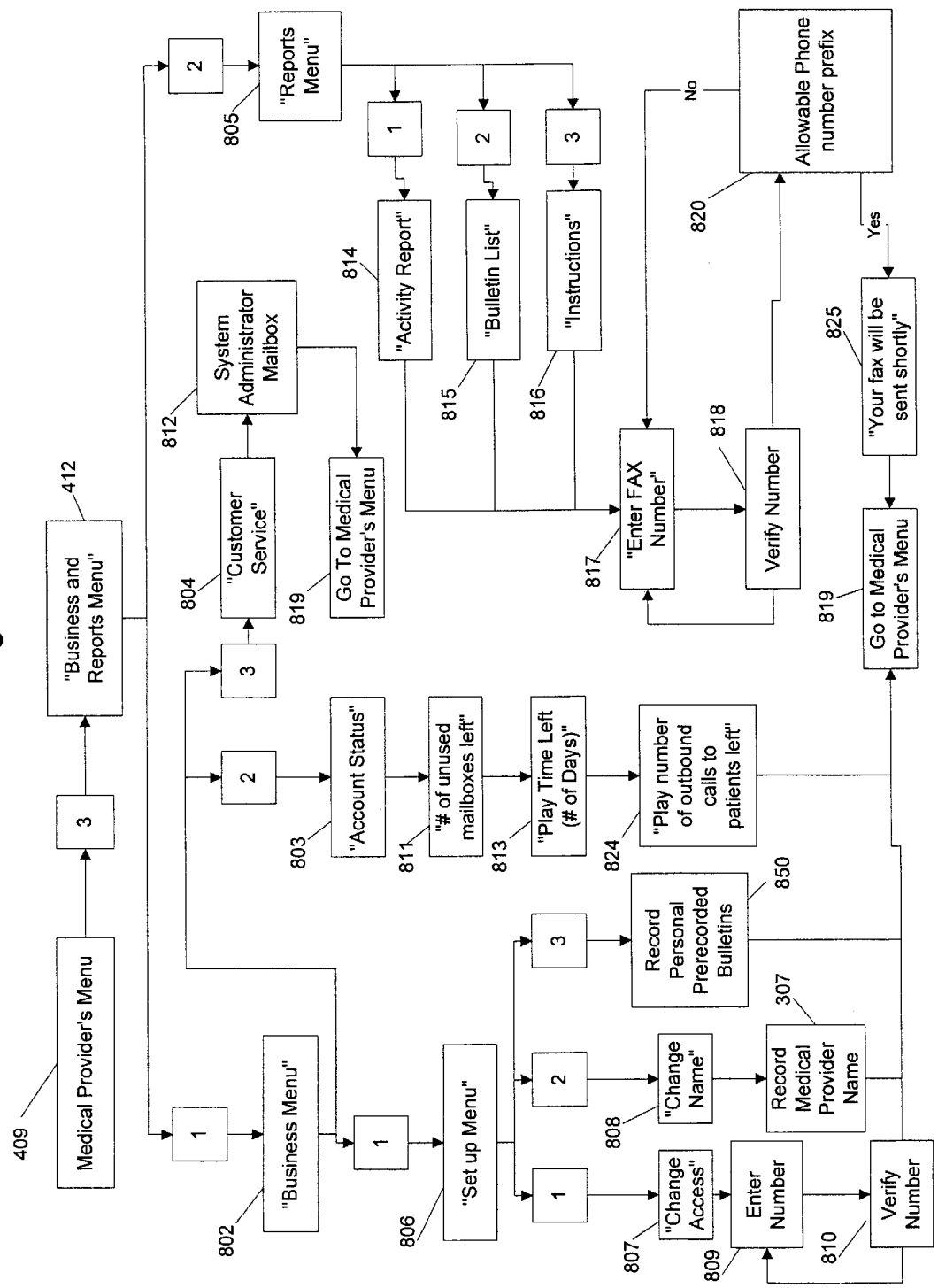
FIG. 8 illustrates a logic flow diagram of providing a) business accounts and reports; b) set-up menu; c) access code definition; d) medical provider name definition; and e) personal prerecorded bulletin definition; in an automated patient information retrieval system according to the present invention.

FIG. 8 illustrates a detailed logic flow diagram of business and report logic block 412 which may be selected by inputting "3" from medical provider's menu logic block 409 as seen in FIG. 4. A medical provider may select either "1" or "2". If the medical provider then selects "1", a business menu message is generated in logic block 802. From this business menu, the medical provider may select "1", "2", or "3". If the medical provider selects "1", a set-up menu message is generated in logic block 806. The medical provider can then select "1", "2" or "3". If the medical provider selects "1", the medical provider may change an access code in logic block 807. A medical provider may then enter a new access number in logic block 809 and verify that number in logic block 810. If the medical provider selects "2" under a set-up menu in logic block 806, the medical provider's name or medical practice name may be changed in logic block 808. The medical provider then may change the name by using the record message function in logic block 307. If the medical provider selects "3" under the setup menu in logic block 806, personal prerecorded bulletins can be recorded in logic block 850.

If the medical provider selects "2" from the business menu in logic block 802, an account status message is generated in logic block 803. The number of unused mailboxes the medical provider has remaining and the number of days paid for remaining on the system are provided in logic blocks 811 and 813, respectively. The number of outbound calls to patients that have been paid for but not used is generated in logic block 824. The physician is also informed on how to obtain additional mailboxes, extend the available time for unused mailboxes or obtain additional outbound calls.

After selecting "3" in business menu 802, a customer service message is prompted in logic block 804. A user then may record a message in a system administrator mailbox in logic block 812.

After selection "2" at the business and reports menu in logic block 412, a reports menu message is generated in logic block 805. A medical provider can generate printouts by selecting "1", "2" or "3". If the medical provider selects "1", an activity report prompt is generated in logic block 814 and an activity prompt report may be faxed or printed. An activity report may include patient ID number, bulletin message code, fill in number value if any, time when a bulletin was created, and time when a patient accessed or picked up the stored message. If a medical provider enters "2", a bulletin code list prompt will be generated in logic block 815 and a bulletin list report may be faxed or printed. A bulletin list includes a list of bulletin code numbers and associated titles. Finally, if the medical provider enters "3", instructions on how to operate system 100 may also be faxed or printed.

It should be understood that while the present invention described transferring information by fax, other transfer devices such as electronic file transfer and recording information on a magnetic or digital (such as CD-ROM) medium may also be used. The medical provider then may enter the fax number where the information will be sent after a prompt in logic block 817. The number will be verified in logic block 818. A determination will then be made whether or not the phone number prefix is allowable in logic block 820. Logic block 825 announces that the fax will be sent shortly and control is then transferred to the Medical Provider's Menu by logic block 819.

Figure 9:
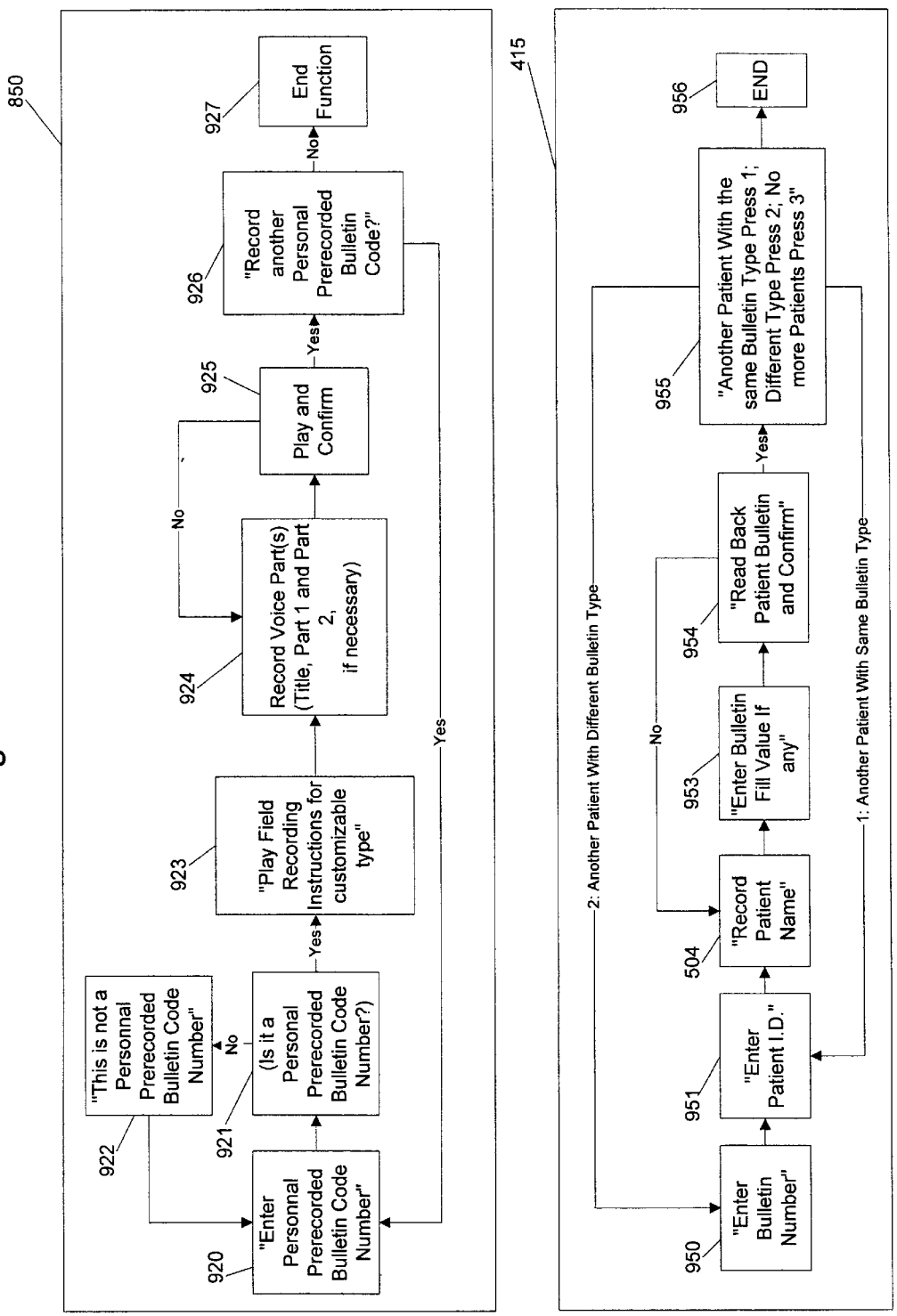
FIG. 9 illustrates a) placing bulletins in multiple patient mailboxes (logic block 415); b) defining a personal prerecorded bulletin (logic block 850); in an automated patient information retrieval system according to the present invention.

FIG. 9 illustrates the logic flow diagram for recording personal prerecorded bulletins by medical providers in logic block 850 and the logic flow diagram for coding multiple bulletins in logic block 415.

In logic block 850 a personal prerecorded message code number as seen in Table B is entered in logic block 920. A determination is made whether the entered code is a valid personal prerecorded number in logic block 921. If the code is not correct logic block 922 transfers control back to logic block 920 for re-entry. The possibilities for the structure of this personal pre-recorded bulletin in terms of the presence or absence of a fill-in number field, the location of the fill-in number field in the bulletin, and formatting information for the fill-in number field are outlined in Table B. In logic block 923, a medical provider is informed of the structure of the field in response to a selected code for the bulletin number. The voice parts or segments to the personal prerecorded bulletin and title are recorded in logic block 924 and then played to confirm in logic block 925. The medical provider is then prompted as to whether or not it is desired to record another personal prerecorded bulletin code in logic block 926. The function ends in logic block 927 if the answer is negative or the medical provider is returned to logic block 920 if additional personal bulletins are to be coded.

In logic block 415, a bulletin may be placed in a plurality of mailboxes. A bulletin number is first entered into logic block 950, followed by the entry of a patient ID in logic block 951. Patient name is entered in logic block 504. Bulletin fill-in value, if any, is entered in logic block 953. Logic block 954 then reads back the created patient bulletin for confirmation. The medical provider is then prompted in logic block 955 to press "1" if the same bulletin for another set of mailboxes is to be created, in which case the program flow is transferred back to logic block 951. If the medical provider presses "2", a different type of bulletin for another set of mailboxes is entered in logic block 950. If the medical provider presses "3", the function ends in logic block 956. If the provider does not confirm the message read in logic block 954, control is transferred back to logic block 504 for re-recording.

FIG. 10 illustrates the database file structure for system 100. In an embodiment, the database file structure comprises database 900, 901, 902 and 903. Each medical provider is assigned four databases. Database 900 consists of unused mailboxes. Databases 901 and 902 are used to generate medical provider reports and can be faxed or downloaded as files. Database 901 includes mailboxes containing medical messages or bulletins that haven't been received or accessed by a patient within a certain predetermined period of time. Database 902 includes mailboxes containing medical messages that have been received or accessed within a predetermined period of time. Finally, database 903 includes voice mailboxes containing medical messages that are older than a predetermined period of time. These mailboxes may be archived on diskette 906. The archived diskette 906 may be used to prove that certain medical messages were available to patients. The information in databases 901 and 902 then may be used to generate reports which may be transferred to medical providers by fax 907, diskette 908, or electronic mail 909.

The foregoing description of the preferred embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents:

What is claimed is:

1. A method for providing a medical voice message in a medical message delivery system, comprising the steps of:

providing a voice mailbox;

generating a medical voice message in the voice mailbox accessible by a patient; and, generating a voice message note by a medical provider associated with the medical voice message, wherein the voice message note is accessible by only the medical provider.

2. The method of claim 1, further comprising the step of:

generating an alert message to a medical provider when the patient has not retrieved the medical voice message in the voice mailbox.

3. The method of claim 1, further comprising the step of:

generating a signal identifying a voice message note.

4. A method for providing status information in an automated patient information retrieval system, comprising the steps of:

obtaining an amount of medical messages entered by a medical provider during a predetermined period of time; and, presenting respective titles associated with the respective medical messages entered.

5. The method of claim 4, further comprising the steps of:

obtaining respective patient names associated with the respective medical messages; and, obtaining respective bulletins associated with the respective medical messages.

6. A method for providing a medical voice message in an automated patient information retrieval system, comprising the steps of:

providing a voice mailbox having a plurality of voice segments;

entering a mailbox number associated with the voice mailbox; and, providing a user a predetermined selection responsive to the mailbox number and contents of a first voice segment in the plurality of voice segments in the voice mailbox.

7. The method of claim 6, wherein the first voice segment is a patient medical message.

8. The method of claim 6, wherein the first voice segment is a medical provider note.

9. The method of claim 6, wherein the first voice segment is a patient name.

10. The method of claim 6, wherein the predetermined selection is a selection in an edit menu.

11. The method of claim 10, wherein a user is presented with multiple choices of editing the plurality of voice segments.

12. The method of claim 6, further comprising the step of:

presenting a medical voice message stored in the voice mailbox.

13. The method of claim 6, further comprising the step of:

presenting a title which summarizes a medical voice message stored in the first voice segment.

14. The method of claim 6, further comprising the steps of:

placing a medical message in the voice mailbox; and, entering alert information into the voice mailbox.

15. The method of claim 6, further comprising the step of:

presenting a medical provider note stored in the first voice segment.

16. The method of claim 6, further comprising the step of:

presenting a patient name stored in the first voice segment.

17. The method of claim 9, further comprising the step of:

presenting alert information, stored in a second voice segment in the plurality of voice segments, associated with the patient name.

18. The method of claim 17, wherein a medical voice message is stored in a second voice segment in the plurality of voice segments, and is categorized in repsonse to the medical voice message being presented to a medical provider.

19. The method of claim 17, wherein a medical voice message is stored in a second voice segment and is categorized in response to the alert information being presented to the medical provider.

20. The method of claim 17, further comprising the step of:

presenting a list of medical voice messages having respective alert information associated with a respective plurality of mailboxes which have been presented to the medical provider.

21. The method of claim 20, further comprising the step of:

removing a medical voice message from the list.

22. The method of claim 17, further comprising the steps of:

presenting a first list of medical voice messages, corresponding to a first category, to a medical provider; and, presenting a second list of medical voice messages, corresponding to a second category, to a medical provider.

23. The method of claim 17, further comprising the step of:

preventing access to a medical voice message, stored in a third voice segment in the plurality of voice segments, responsive to the medical voice message being presented to the patient.

24. The method of claim 6, further comprising the steps of:

placing the medical message in the voice mailbox; and, entering contact information in the voice mailbox.

25. The method of claim 6, further comprising the steps of:

entering alert information in the voice mailbox; and, entering contact information in the voice mailbox.

26. The method of claim 17, further comprising the steps of:

presenting a list of titles of medical voice messages having respective alert information associated with the respective plurality of mailboxes which have been presented to the medical provider.

* * * * *